(12) United States Patent
Sahu

(10) Patent No.: US 7,855,005 B2
(45) Date of Patent: Dec. 21, 2010

(54) APPARATUS AND METHODS OF DETERMINATION OF STATE OF CHARGE IN A REDOX FLOW BATTERY

(75) Inventor: Saroj Kumar Sahu, Fremont, CA (US)

(73) Assignee: Deeya Energy, Inc., Fremont, CA (US)

( * ) Notice: Subject to any disclaimer, the term of this patent is extended or adjusted under 35 U.S.C. 154(b) by 983 days.

(21) Appl. No.: 11/674,101

(22) Filed: Feb. 12, 2007

(65) Prior Publication Data

US 2008/0193828 A1 Aug. 14, 2008

(51) Int. Cl.
*H01M 2/38* (2006.01)
*H01M 10/48* (2006.01)
*H02J 7/00* (2006.01)
*B23H 3/02* (2006.01)

(52) U.S. Cl. .............................. 429/51; 429/63; 429/90; 429/91; 320/134; 320/137; 324/432; 204/228.6

(58) Field of Classification Search ................... 429/63, 429/61, 91, 90, 92, 50, 51; 320/136, 134, 320/137, DIG. 21; 324/425, 426, 432, 435; 356/6, 36, 72, 303, 319; 204/450, 228.6; 422/82.09

See application file for complete search history.

(56) References Cited

U.S. PATENT DOCUMENTS

| | | |
|---|---|---|
| 3,540,934 A | 11/1970 | Boeke |
| 3,996,064 A | 12/1976 | Thaller |
| 4,133,941 A | 1/1979 | Sheibley |
| 4,159,366 A | 6/1979 | Thaller |
| 4,309,372 A | 1/1982 | Sheibley |
| 4,312,735 A | 1/1982 | Grimes et al. |
| 4,414,090 A | 11/1983 | D'Agostino et al. |
| 4,454,649 A | 6/1984 | Jalan et al. |
| 4,468,441 A | 8/1984 | D'Agostino et al. |
| 4,485,154 A | 11/1984 | Remick et al. |
| 4,496,637 A | 1/1985 | Shimada et al. |
| 4,543,302 A | 9/1985 | Gahn et al. |
| 4,732,827 A | 3/1988 | Kaneko et al. |
| 4,784,924 A | 11/1988 | Savinell et al. |
| 4,814,241 A | 3/1989 | Nagashima et al. |
| 4,828,666 A | 5/1989 | Iizuka et al. |
| 4,874,483 A | 10/1989 | Wakabayashi et al. |

(Continued)

FOREIGN PATENT DOCUMENTS

DE 102006007206 10/2006

(Continued)

OTHER PUBLICATIONS

International Search Report and the Written Opinion mailed Jul. 22, 2008, in related international application No. PCT/US08/53601.

(Continued)

*Primary Examiner*—Raymond Alejandro
(74) *Attorney, Agent, or Firm*—Haynes and Boone, LLP

(57) ABSTRACT

Methods for determining the state of charge of an electrolyte solution in a redox battery by optical absorption spectrophotometry are disclosed. The state of charge thus obtained may serve as a gauge for the amount of electro-chemical energy left in the system.

18 Claims, 10 Drawing Sheets

U.S. PATENT DOCUMENTS

| | | | |
|---|---|---|---|
| 4,882,241 | A | 11/1989 | Heinzel |
| 4,894,294 | A | 1/1990 | Ashizawa et al. |
| 4,929,325 | A | 5/1990 | Bowen et al. |
| 4,945,019 | A | 7/1990 | Bowen et al. |
| 4,948,681 | A | 8/1990 | Zagrodnik et al. |
| 4,956,244 | A | 9/1990 | Shimizu et al. |
| 5,061,578 | A | 10/1991 | Kozuma et al. |
| 5,119,011 | A | 6/1992 | Lambert |
| 5,162,168 | A | 11/1992 | Downing et al. |
| 5,188,911 | A | 2/1993 | Downing et al. |
| 5,258,241 | A | 11/1993 | Ledjeff et al. |
| 5,366,824 | A | 11/1994 | Nozaki et al. |
| 5,648,184 | A | 7/1997 | Inoue et al. |
| 5,656,390 | A | 8/1997 | Kageyama et al. |
| 5,665,212 | A | 9/1997 | Zhong et al. |
| 5,759,711 | A | 6/1998 | Miyabayashi et al. |
| 5,847,566 | A | 12/1998 | Marritt et al. |
| 5,851,694 | A | 12/1998 | Miyabayashi et al. |
| 5,949,219 | A * | 9/1999 | Weiss ............... 320/136 |
| 6,005,183 | A | 12/1999 | Akai et al. |
| 6,037,749 | A | 3/2000 | Parsonage |
| 6,040,075 | A | 3/2000 | Adcock et al. |
| 6,086,643 | A | 7/2000 | Clark et al. |
| 6,461,772 | B1 | 10/2002 | Miyake et al. |
| 6,475,661 | B1 | 11/2002 | Pellegri et al. |
| 6,509,119 | B1 | 1/2003 | Kobayashi et al. |
| 6,524,452 | B1 | 2/2003 | Clark et al. |
| 6,555,267 | B1 | 4/2003 | Broman et al. |
| 6,562,514 | B1 | 5/2003 | Kazacos et al. |
| 6,692,862 | B1 | 2/2004 | Zocchi |
| 6,759,158 | B2 | 7/2004 | Tomazic |
| 6,761,945 | B1 | 7/2004 | Adachi et al. |
| 6,764,789 | B1 | 7/2004 | Sekiguchi et al. |
| 6,905,797 | B2 | 6/2005 | Broman et al. |
| 6,940,255 | B2 | 9/2005 | Loch |
| 6,986,966 | B2 | 1/2006 | Clarke et al. |
| 7,061,205 | B2 | 6/2006 | Shigematsu et al. |
| 7,078,123 | B2 | 7/2006 | Kazacos et al. |
| 7,199,550 | B2 | 4/2007 | Tsutsui et al. |
| 7,220,515 | B2 | 5/2007 | Ito et al. |
| 7,227,275 | B2 | 6/2007 | Hennessy et al. |
| 2003/0008203 | A1 | 1/2003 | Winter |
| 2004/0170893 | A1 | 9/2004 | Nakaishi et al. |
| 2004/2002915 | | 10/2004 | Nakaishi et al. |
| 2004/0241544 | A1 | 12/2004 | Nakaishi et al. |
| 2005/0074653 | A1 | 4/2005 | Broman et al. |
| 2005/0156431 | A1 | 7/2005 | Hennessy |
| 2005/0156432 | A1 | 7/2005 | Hennessy |
| 2005/0158615 | A1 | 7/2005 | Samuel et al. |
| 2005/0164075 | A1 | 7/2005 | Kumamoto et al. |
| 2005/0181273 | A1 | 8/2005 | Deguchi et al. |
| 2005/0260473 | A1 | 11/2005 | Wang |
| 2007/0072067 | A1 | 3/2007 | Symons et al. |
| 2007/0080666 | A1 | 4/2007 | Ritter et al. |
| 2007/0111089 | A1 | 5/2007 | Swan |
| 2010/0003586 | A1 | 1/2010 | Sahu |
| 2010/0090651 | A1 | 4/2010 | Sahu |
| 2010/0092807 | A1 | 4/2010 | Sahu |
| 2010/0092813 | A1 | 4/2010 | Sahu |
| 2010/0092843 | A1 | 4/2010 | Conway |
| 2010/0094468 | A1 | 4/2010 | Sahu |
| 2010/0136455 | A1 | 6/2010 | Winter |

FOREIGN PATENT DOCUMENTS

| | | |
|---|---|---|
| JP | 60047373 | 3/1985 |
| JP | 60070672 | 4/1985 |
| JP | 60115174 | 6/1985 |
| JP | 1060967 | 3/1989 |
| JP | 1320776 | 12/1989 |
| JP | 2027667 | 1/1990 |
| JP | 2027668 | 1/1990 |
| JP | 3017963 | 1/1991 |
| JP | 8007913 | 1/1996 |
| JP | 10012260 | 1/1998 |
| JP | 10208766 | 8/1998 |
| JP | 11329474 | 11/1999 |
| JP | 2000058099 | 2/2000 |
| JP | 2000200619 | 7/2000 |
| JP | 2002015762 | 1/2002 |
| JP | 2002175822 | 6/2002 |
| JP | 2002289233 | 10/2002 |
| JP | 2002367661 | 12/2002 |
| JP | 2003173812 | 6/2003 |
| JP | 2005142056 | 6/2005 |
| JP | 2005228622 | 8/2005 |
| JP | 2005228633 | 8/2005 |
| JP | 2005322447 | 11/2005 |
| JP | 2006107988 | 4/2006 |
| JP | 2006114360 | 4/2006 |
| JP | 2006147306 | 6/2006 |
| JP | 2006147376 | 6/2006 |
| JP | 2006313691 | 11/2006 |
| JP | 2006351346 | 12/2006 |
| JP | 2007087829 | 4/2007 |
| WO | 8905528 | 6/1989 |
| WO | WO 90/03666 | 4/1990 |
| WO | 03005476 | 1/2003 |
| WO | 2004079849 | 9/2004 |
| WO | 2006135958 | 12/2006 |

OTHER PUBLICATIONS

Search Report for PCT Application No. PCT/US2009/060279.

* cited by examiner

APPARATUS AND METHODS OF DETERMINATION OF STATE OF CHARGE IN A REDOX FLOW BATTERY

BACKGROUND OF THE INVENTION

The present invention relates to the field of measurements and in particular to apparatus and methods for optically measuring the state of charge of at least one electrolyte.

The present invention relates generally to reduction-oxidation, or redox flow batteries used to store electrical energy in a chemical form, and subsequently dispense the stored energy in an electrical form via a spontaneous reverse redox reaction. Aspects of redox flow batteries incorporating external liquid electrolytes have been described (see for example Thaller, U.S. Pat. No. 3,996,064, herein incorporated by reference).

A redox flow battery is an electrochemical storage device in which an electrolyte containing one or more dissolved electroactive species flows through a reactor converting chemical energy to electrical energy and vice versa. Additional electrolyte is stored externally, (for example in tanks) and flows through a set of cells (e.g. by pumps, gravity or other movement) where the electrochemical reaction takes place. Typically, the reaction in a flow battery is reversible, i.e. it can be recharged without replacing the electroactive material. The energy capacity of a redox flow battery is related to the electrolyte volume (tank size). The discharge time of a redox flow battery at full power varies from several minutes to many days. Advantages of flow cells over standard fuel cells and batteries may include some or all of flexible device layout (due to separation of the power and energy components), long cycle life (because there are no solid-solid phase changes), no harmful emissions are generated, low maintenance and tolerance to overcharge/overdischarge. Disadvantages may include their complicated apparatus, (requiring pumps, sensors, control units, secondary containment vessels, etc) and low energy densities.

A flow battery differs from a secondary battery in the sense that flow batteries maintain the majority of the electrolyte outside of the cell volume, pumping it into the cell as needed. Hence the power and energy capacity are decoupled. Secondary batteries retain all of the electrolyte within the cell volume, and hence the power and energy capacity are coupled. However, both a flow battery and a secondary battery are rechargeable.

A flow battery differs from a fuel cell in the sense that although both work on electrochemical redox principles, in the latter a fuel is generally consumed and the system is generally not rechargeable. Conventional fuel cell fuels include hydrogen, methanol, gasoline, etc. The fuel must be continuously replenished in order to produce power. The electrolytes in a flow battery are rechargeable, and therefore an external fuel supply is unnecessary.

It may be noted that the minimal unit that performs electrochemical energy conversion is generally called a "cell", whether in the case of flow batteries, fuel cells or secondary batteries. A device that integrates many such cells, in series or parallel, to obtain higher current or voltage or both, is generally referred to as a "battery". However, it is common to refer to a single cell used on its own as a battery rather than a cell, thus leading to some possible confusion.

The redox flow cell works by changing the oxidation state of its constituents during charging or discharging. The basic cell consists of two half-cells, connected in series by the conductive electrolyte, one for anodic reaction and the other for cathodic reaction. Each half-cell comprises an electrode with a defined surface area upon which the redox reaction takes place. Electrolyte flows through the half-cell as the redox reaction takes place. The two half-cells are separated by an ion-exchange membrane that allows primarily either positive ions or negative ions to pass through it. Multiple such cells can be stacked either in series to achieve higher voltage or in parallel in order to achieve higher current. The reactants are stored in separate tanks and dispensed into the cells as necessary in a controlled manner.

A non limiting, illustrative example of a Redox pair would include:

$$Fe^{3+}+e^- \rightarrow Fe^{2+}(E_o=+0.771V)$$

$$Cr^{3+}+e^- \rightarrow Cr^{2+}(E_o=-0.407V)$$

where $E_o$ is the standard electrode potential of the reaction.

If the electrolyte has a net higher positive electrode potential ($E_o$) compared to a Standard Hydrogen Electrode (SHE) during discharge of the system, then the electrolyte is called the catholyte. The complementary electrolyte is then called the anolyte.

In a simple implementation of the redox cell technology, an acidic solution of $FeCl_2$ is on the cathode side and an acidic solution of $CrCl_3$ is on the anode side. Upon applying an appropriate positive voltage on the cathode with respect to the anode, the following reactions take place:

$$\text{Cathodic reaction: } Fe^{2+} \rightarrow Fe^{3+}+e^-$$

$$\text{Anodic reaction: } Cr^{3+}+e^- \rightarrow Cr^{2+}$$

Applying the external power supply affects an electron transfer, while a $Cl^-$ ion crosses the membrane from the anodic half-cell to the cathodic half-cell through the ion exchange membrane in order to preserve the charge balance. In the ideal situation, the fully charged flow cell consists of 100% $FeCl_3$ solution on the cathode side and 100% $CrCl_2$ solution on the anode side.

When the external power supply is replaced with a load, the cell begins to discharge, and the opposite Redox reactions take place:

$$\text{Cathodic reaction: } Fe^{3+}+e^- \rightarrow Fe^{2+}$$

$$\text{Anodic reaction: } Cr^{2+} \rightarrow Cr^{3+}+e^-$$

Therefore, in the most ideal situation, the fully discharged flow cell consists of 100% $FeCl_2$ solution on the cathode side and 100% $CrCl_3$ solution on the anode side.

A variation of the Fe/Cr system described above is a redox cell with premixed Fe and Cr solutions (see Gahn et al, NASA TM-87034). Since no membrane is perfectly perm-selective, anolyte and catholyte eventually become cross-mixed over many cycles of charge and discharge, thus reducing the net system capacity. Gahn et al proposed a remedy to this problem using a redox cell, both sides of which contain $FeCl_2$ and $CrCl_3$ solutions in 1:1 proportion in the completely discharged state. In the completely charged state, the anolyte comprises $CrCl_2$ and $FeCl_2$ in 1:1 proportion and the catholyte comprises $FeCl_3$ and $CrCl_3$ in 1:1 proportion. In this way, any cross-diffusion of species merely appears as a Coulombic inefficiency, and over time the 1:1 charge balance is maintained. Although the above example describes a Fe/Cr system, it is generally applicable to other Redox couples, such as for example all-Vanadium systems, (see Skyllas-Kazacos in U.S. Pat. No. 4,786,567, incorporated by reference).

One of the major problems of such redox cells is maintaining the charge balance between the anodic and cathodic sides of the cell. If there are no parasitic reactions other than the fundamental redox reactions, then the two sides are always in a charge balanced state. However, in reality parasitic reactions do occur, and after many cycles of charge and discharge, a marked difference with respect to the state of charge of the two electrolyte solutions may develop.

Using the Fe/Cr system as a non limiting example, under ideal conditions (i.e. no parasitic reactions occur) for every $Fe^{3+}$ ion in the cathode tank there is a $Cr^{2+}$ ion in the anode tank, and for every $Fe^{2+}$ ion in the cathode tank, there is a $Cr^{3+}$ ion in the anode tank. However, in practice, during the charging process, though $Fe^{2+}$ oxidation proceeds with nearly 100% current yield, reduction of $Cr^{3+}$ generates hydrogen as a side reaction on the graphite electrodes (see for example U.S. Pat. No. 3,996,064, U.S. Pat. No. 4,382,116 and EPO 0312875), resulting in a higher state of charge of the iron electrolyte i.e. in an excess of $Fe^{3+}$ ions. Other examples of parasitic reactions include, oxygen (internal or external to the system) oxidizing $Fe^{2+}$ to $Fe^{3+}$, or $Cr^{2+}$ to $Cr^{3+}$; $Cr^{2+}$ reducing water to become $Cr^{3+}$; or during charging, hydrogen generation on the anode in competition with $Cr^{3+}$ reduction, while $Fe^{2+}$ oxidation takes place on the cathode.

When this charge imbalance occurs, a rebalancing mechanism is required to return the electrolytes to their charge balanced state. Various rebalancing methods are known to those in the art. Again, using the Fe/Cr system as a non limiting example, charge rebalancing may be achieved by reducing $Fe^{3+}$ to $Fe^{2+}$ with hydrogen, (see Thaller in U.S. Pat. No. 4,159,366, herein incorporated by reference).

Before such a rebalancing measure should be taken, it is important to know the state of charge on each side of the cell. Otherwise, an act of unnecessary rebalancing may lead to a worse state of balance and/or waste of energy.

Typically, the state of the charge is determined using separate Open Circuit Voltage (OCV) cell, as described by Hagedorn and Thaller (NASA/TM-81464). The OCV cell is the same as the Redox cell except that there is very high load impedance across the electrodes. Voltage is measured across this resistance, and as the current is virtually zero, it is very close to the OCV, which in turn is directly related to the concentrations of the reactants through Nernst Equation:

$$OCV = E_{o} - 0.0592 Ln \frac{[Cr^{3+}][Fe^{2+}]}{[Cr^{2+}][Fe^{3+}]}$$

where $E_o$ is the standard potential. Measurement of the OCV is therefore an indirect measurement of the ratio of reactants in the system. However, measuring the OCV in order to determine the charge balance of the redox system has its limitations. For example, it is difficult to differentiate between a system that is out of balance due to parasitic reactions from a partially discharged system. To overcome this limitation one would have to have an accurate coulomb gauge in place, which in turn may be subject to cumulative error after many cycles of operation and the presence of an internal shunt current generated through conductive liquid paths across cells.

Alternatively, it is possible to measure the state of charge of the anode and cathode tanks independently by using cells with respect to standard electrodes, such as Pt/H2 or Ag/AgCl, commonly used in the field of electrochemistry. However, such in situ methods have short life spans, due to the contamination and consumption of the standard electrodes, requiring their frequent replacement. Additionally, cross diffusion of reactants into opposite half-cells renders these measurements unreliable. Further, in premixed solution redox cells, as noted earlier it becomes even more difficult to measure the state of charge and state of balance by just measuring the OCV, as there are many reactants and unknown concentrations involved in the Nernst Equation. Even when reactants are unmixed, cross-diffusion renders the calculation of state of charge and state of balance from OCV erroneous.

It is therefore highly desirable in a redox flow cell system to have a reliable method for determining the state of charge of each electrolyte and the overall state of charge balance, independent of any electrochemical measurement.

SUMMARY OF THE INVENTION

Described herein are redox flow batteries comprised of at least one anolyte and at least one catholyte. Also described herein are the apparatus and methods for determining the state of charge of the at least one anolyte and at least one catholyte of the redox flow batteries. Further described herein are the apparatus and methods for determining the state of charge balance between the at least one anolyte and at least one catholyte of the redox flow batteries. Further described herein are the apparatus and methods for determining if a redox system is out of electrolyte charge balance and, if the redox system is found to be out of charge balance, methods for restoring the electrolyte charge balance of the redox system.

In some embodiments, the redox flow batteries comprise at least one anolyte having different optical absorption spectra in reduced and oxidized forms, at least one catholyte having different optical absorption spectra in reduced and oxidized forms, and a spectrophotometer for independently measuring the optical absorption spectra of said anolyte and said catholyte. In further or additional embodiments, the at least one catholyte comprises an acidic solution. In further or additional embodiments, the acidic catholyte solution comprises hydrochloric acid, hydrobromic acid or a mixture thereof. In further or additional embodiments, the acidic catholyte solution further comprises aqueous metal chloride salts. In further or additional embodiments the absorption wavelength of the catholyte is greater than about 750 nm. In further or additional embodiments, the at least one anolyte comprises an acidic solution. In further or additional embodiments, the acidic anolyte solution comprises hydrochloric acid, hydrobromic acid or a mixture thereof. In further or additional embodiments, the acidic anolyte solution further comprises aqueous metal chloride salts. In further or additional embodiments the absorption wavelength of the anolyte is between about 400 nm and 700 nm or between about 730 nm and 1100 nm. In some embodiments the concentrations of at the least one anolyte and the at least one catholyte solutions are different. In further or additional embodiments the concentrations of at least one anolyte and at least one catholyte solutions are substantially the same. In further or additional embodiments the concentrations of at least one anolyte and at least one catholyte solutions are the same. In yet other embodiments the concentrations of at the least one anolyte and the at least one catholyte solutions are at least 0.1M. In further or additional embodiments the concentrations of at the least one anolyte and the at least one catholyte solutions are at least 0.2M. In further or additional embodiments the concentrations of at the least one anolyte and the at least one catholyte solutions are at least 0.5M. In further or additional embodiments the concentrations of at the least one anolyte and the at least one catholyte solutions are from about 0.1M to about 15M. In further or additional embodiments the concentrations of at the least one anolyte and at least one catholyte solutions are from about 0.2M to about 10M. In further or additional embodiments the concentrations of at the least one anolyte and the at least one catholyte solutions are from about 0.5M to about 8M. In some embodiments the anolyte comprises an acidic solution comprising $Cr^{2+}$, $Cr^{3+}$ and $Fe^{2+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state. In some embodiments the catholyte comprises an acidic solution comprising $Fe^{2+}$, $Fe^{3+}$ and $Cr^{3+}$. In further or additional embodiments the catholyte comprises an acidic solution comprising $Cr^{3+}$ and $Fe^{3+}$ in the completely charged state and $Cr^{3+}$ and $Fe^{2+}$ in the completely discharged state. In some embodiments the anolyte comprises an acidic solution comprising $Cr^{2+}$, $Cr^{3+}$ and $Fe^{2+}$ and the catholyte comprises an acidic solution comprising $Fe^{2+}$, $Fe^{3+}$ and $Cr^{3+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state and the catholyte comprises an acidic solution comprising $Cr^{3+}$ and $Fe^{3+}$ in the completely charged state and $Cr^{3+}$ and $Fe^{2+}$ in the completely discharged state. In some embodiments the spectrophotometer comprises at least one light emitter and at least one light receiver. In further or additional embodiments the light emitters of the spectrophotometer are Light Emitting Diodes (LEDs). In further or additional embodiments the light emitters of the spectrophotometer emit light as photometric beams with spectral bandwidths less than about 50 nm at FWHM (Full Width at Half Maximum). In further or additional embodiments the spectrophotometer comprises two light emitters. In further or additional embodiments the spectrophotometer comprises two light emitters, wherein one light emitter is for anolyte photometry and one light emitter is for catholyte photometry. In further or additional embodiments the anolyte light emitter emits light of wavelength from about 700 nm to about 1000 nm and the catholyte light emitter emits light of wavelength from about 800 nm to about 1000 nm. In some embodiments the light receiver of the spectrophotometer further comprises at least one filter. In further or additional embodiments the filter filters incoming photometric beams to produce incoming photometric beams with spectral bandwidths less than about 50 nm at FWHM (Full Width at Half Maximum). In some embodiments the redox flow battery further comprises at least one transparent tube. In further or additional embodiments the at least one transparent tube intercepts at least one of the photometric beams. In further or additional embodiments at least one electrolyte flows through at least one of the transparent tubes. In further or additional embodiments the at least one transparent tube is curved. In further or additional embodiments the curvature of at least one of the transparent tubes imparts a lensing effect on at least one of the photometric beams. In further or additional embodiments said lensing effect increases the photometric density of light falling on the detector, resulting in an increase in the signal-to-noise ratio of the photometric measurement.

Also described are redox flow batteries comprising at least one anolyte having different optical absorption spectra in reduced and oxidized forms, at least one catholyte having different optical absorption spectra in reduced and oxidized forms, a spectrophotometer for independently measuring the optical absorption spectra of said anolyte and said catholyte and a rebalance mechanism that reduces or oxidizes either said anolyte or said catholyte or both, when a charge imbalance between said anolyte and catholyte is detected. In further or additional embodiments, the at least one catholyte comprises an acidic solution. In further or additional embodiments, the acidic catholyte solution comprises hydrochloric acid, hydrobromic acid or a mixture thereof. In further or additional embodiments, the acidic catholyte solution further comprises aqueous metal chloride salts. In further or additional embodiments the absorption wavelength of the catholyte is greater than about 750 nm. In further or additional embodiments, the at least one anolyte comprises an acidic solution. In further or additional embodiments, the acidic anolyte solution comprises hydrochloric acid, hydrobromic acid or a mixture thereof. In further or additional embodiments, the acidic anolyte solution further comprises aqueous metal chloride salts. In further or additional embodiments the absorption wavelength of the anolyte is between about 400 nm and 700 nm or between about 730 nm and 1100 nm. In some embodiments the concentrations of at the least one anolyte and the at least one catholyte solutions are different. In further or additional embodiments the concentrations of at least one anolyte and at least one catholyte solutions are substantially the same. In further or additional embodiments the concentrations of at least one anolyte and at least one catholyte solutions are the same. In yet other embodiments the concentrations of at the least one anolyte and the at least one catholyte solutions are at least 0.1M. In further or additional embodiments the concentrations of at the least one anolyte and the at least one catholyte solutions are at least 0.2M. In further or additional embodiments the concentrations of at the least one anolyte and the at least one, catholyte solutions are at least 0.5M. In further or additional embodiments the concentrations of at the least one anolyte and the at least one catholyte solutions are from about 0.1M to about 15M. In further or additional embodiments the concentrations of at the least one anolyte and the at least one catholyte solutions are from about 0.2M to about 10M. In further or additional embodiments the concentrations of at the least one anolyte and the at least one catholyte solutions are from about 0.5M to about 8M. In some embodiments the anolyte comprises an acidic solution comprising $Cr^{2+}$, $Cr^{3+}$ and $Fe^{2+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state. In some embodiments the catholyte comprises an acidic solution comprising $Fe^{2+}$, $Fe^{3+}$ and $Cr^{3+}$. In further or additional embodiments the catholyte comprises an acidic solution comprising $Cr^{3+}$ and $Fe^{3+}$ in the completely charged state and $Cr^{3+}$ and $Fe^{2+}$ in the completely discharged state. In some embodiments the anolyte comprises an acidic solution comprising $Cr^{2+}$, $Cr^{3+}$ and $Fe^{2+}$ and the catholyte comprises an acidic solution comprising $Fe^{2+}$, $Fe^{3+}$ and $Cr^{3+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state and the catholyte comprises an acidic solution comprising $Cr^{3+}$ and $Fe^{3+}$ in the completely charged state and $Cr^{3+}$ and $Fe^{2+}$ in the completely discharged state. In some embodiments the spectrophotometer comprises at least one light emitter and at least one light receiver. In further or additional embodiments the light emitters of the spectrophotometer are Light Emitting Diodes (LEDs). In further or additional embodiments the light emitters of the spectrophotometer emit light as photometric beams with spectral bandwidths less than about 50 nm at FWHM (Full Width at Half Maximum). In further or additional embodiments the spectrophotometer comprises two light emitters. In further or additional embodiments the spectrophotometer comprises two light emitters, wherein one light emitter is for anolyte photometry and one light emitter is for catholyte photometry. In further or additional embodiments the anolyte light emitter emits light of wavelength from about 700 nm to about 1000 nm and the catholyte light emitter emits light of wavelength from about 800 nm to about 1000 nm. In some embodiments the light receiver of the spectrophotometer further comprises at least one filter. In further or additional embodiments the filter filters incoming photometric beams to produce incoming photometric beams with spectral bandwidths less than about 50 nm at FWHM (Full Width at Half Maximum). In some embodiments the redox flow battery further comprises at least one transparent tube. In further or additional embodiments the at least one transparent tube intercepts at least one of the photometric beams. In further or additional embodiments at least one electrolyte flows through at least one of the transparent tubes. In further or additional embodiments the at least one transparent tube is curved. In further or additional embodiments the curvature of at least one of the transparent tubes imparts a lensing effect on at least one of the photometric beams. In further or additional embodiments said lensing effect increases the photometric density of light falling on the detector, resulting in an increase in the signal-to-noise ratio of the photometric measurement.

Also described herein are electrolyte rebalancing, electrical energy storage systems comprising a redox flow battery comprising a first electrolyte that exhibits a first optical absorption spectra and a second electrolyte that exhibits a second optical absorption spectra, a spectrophotometer for measuring said first and second optical absorption spectra of said first and second electrolyte respectively, a means for correlating said first and second optical absorption spectra with the state of charge of said first and second electrolyte respectively and a rebalance mechanism for restoring charge balance when a charge imbalance is detected as between said first and second electrolytes as determined by their respective optical absorption spectra. In further or additional embodiments, the first electrolyte comprises an acidic solution. In further or additional embodiments, the acidic electrolyte solution comprises hydrochloric acid, hydrobromic acid or a mixture thereof. In further or additional embodiments, the acidic electrolyte solution further comprises aqueous metal chloride salts. In further or additional embodiments the absorption wavelength of the first electrolyte is greater than about 750 nm. In further or additional embodiments, the second electrolyte comprises an acidic solution. In further or additional embodiments, the acidic electrolyte solution comprises hydrochloric acid, hydrobromic acid or a mixture thereof. In further or additional embodiments, the acidic electrolyte solution further comprises aqueous metal chloride salts. In further or additional embodiments the absorption wavelength of the second electrolyte is between about 400 nm and 700 nm or between about 730 nm and 1100 nm. In some embodiments the concentrations of the first and second electrolyte solutions are different. In further or additional embodiments the concentrations of the first and second electrolyte solutions are substantially the same. In further or additional embodiments the concentrations of the first and second electrolyte solutions are the same. In yet other embodiments the concentrations of the concentrations of the first and second electrolyte solutions are at least 0.1M. In further or additional embodiments the concentrations of the first and second electrolyte solutions are at least 0.2M. In further or additional embodiments the concentrations of the first and second electrolyte solutions are at least 0.5M. In further or additional embodiments the concentrations of the first and second electrolyte solutions are from about 0.1M to about 15M. In further or additional embodiments the concentrations of the first and second electrolyte solutions are from about 0.2M to about 10M. In further or additional embodiments the concentrations of the first and second electrolyte solutions are from about 0.5M to about 8M. In some embodiments the first electrolyte is an anolyte. In other embodiments the first electrolyte is a catholyte. In some embodiments, the second electrolyte is an anolyte. In other embodiments the second electrolyte is a catholyte. In some embodiments the anolyte comprises an acidic solution comprising $Cr^{2+}$, $Cr^{3+}$ and $Fe^{2+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state. In some embodiments the catholyte comprises an acidic solution comprising $Fe^{2+}$, $Fe^{3+}$ and $Cr^{3+}$. In further or additional embodiments the catholyte comprises an acidic solution comprising $Cr^{3+}$ and $Fe^{3+}$ in the completely charged state and $Cr^{3+}$ and $Fe^{2+}$ in the completely discharged state. In some embodiments the anolyte comprises an acidic solution comprising $Cr^{2+}$, $Cr^{3+}$ and $Fe^{2+}$ and the catholyte comprises an acidic solution comprising $Fe^{2+}$, $Fe^{3+}$ and $Cr^{3+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state and the catholyte comprises an acidic solution comprising $Cr^{3+}$ and $Fe^{3+}$ in the completely charged state and $Cr^{3+}$ and $Fe^{2+}$ in the completely discharged state. In some embodiments the spectrophotometer comprises at least one light emitter and at least one light receiver. In further or additional embodiments the light emitters of the spectrophotometer are Light Emitting Diodes (LEDs). In further or additional embodiments the light emitters of the spectrophotometer emit light as photometric beams with spectral bandwidths less than about 50 nm at FWHM (Full Width at Half Maximum). In further or additional embodiments the spectrophotometer comprises two light emitters. In further or additional embodiments the spectrophotometer comprises two light emitters, wherein one light emitter is for anolyte photometry and one light emitter is for catholyte photometry. In further or additional embodiments the anolyte light emitter emits light of wavelength from about 700 nm to about 1000 nm and the catholyte light emitter emits light of wavelength from about 800 nm to about 1000 nm. In some embodiments the light receiver of the spectrophotometer further comprises at least one filter. In further or additional embodiments the filter filters incoming photometric beams to produce incoming photometric beams with spectral bandwidths less than about 50 nm at FWHM (Full Width at Half Maximum). In some embodiments the electrolyte rebalancing, electrical energy storage system further comprises at least one transparent tube. In further or additional embodiments the electrolyte rebalancing, electrical energy storage system further comprises two transparent tubes. In further or additional embodiments the at least one transparent tube intercepts at least one of the photometric beams. In further or additional embodiments the first electrolyte flows through one transparent tube. In further or additional embodiments the second electrolyte flows through one transparent tube. In further or additional embodiments the redox system further comprises two transparent tubes wherein the first electrolyte flows through one transparent tube and the second electrolyte flows a second transparent tube. In further or additional embodiments the at least one transparent tube is curved. In further or additional embodiments the curvature of at least one of the transparent tubes imparts a lensing effect on at least one of the photometric beams. In further or additional embodiments said lensing effect increases the photometric density of light falling on the detector, resulting in an increase in the signal-to-noise ratio of the photometric measurement. In some embodiments the means for correlating said first and second optical absorption spectra with the state of charge of said first and second electrolyte uses analog circuits, application specific integrated circuits (ASICs), mixed signal circuits, algorithms, look up tables, correlation tables, correlation graphs or any combination thereof.

Also described are electrolyte state of charge measuring systems comprising at least one electrolyte having different optical absorption spectra in reduced and oxidized forms, a spectrophotometer for measuring the optical absorption spectra of the at least one electrolyte, a means for correlating the optical absorption spectra of the at least one electrolyte with the state of charge of said electrolyte and an output for providing the state of charge to the system. In some embodiments, the electrolyte comprises an acidic solution. In further or additional embodiments, the acidic electrolyte solution comprises hydrochloric acid, hydrobromic acid or a mixture thereof. In further or additional embodiments, the acidic electrolyte solution further comprises aqueous metal chloride salts. In further or additional embodiments the absorption wavelength of the electrolyte is between about 400 nm and 700 nm, between about 730 nm and 1100 nm or is greater than about 750 nm. In some embodiments the concentration of the electrolyte solution is at least 0.1M. In further or additional embodiments the concentration of the electrolyte solution is at least 0.2M. In further or additional embodiments the concentration of the electrolyte solution is at least 0.5M. In further or additional embodiments the concentration of the electrolyte solution is from about 0.1M to about 15M. In further or additional embodiments the concentration of the electrolyte solution is from about 0.2M to about 10M. In further or additional embodiments the concentration of the electrolyte solution is from about 0.5M to about 8M. In some embodiments the electrolyte comprises an acidic solution comprising $Cr^{2+}$, $Cr^{3+}$ and $Fe^{2+}$. In further or additional embodiments the electrolyte comprises an acidic solution comprising $Cr^{2+}$ and $Fe^{2+}$ in the completely charged state and $Cr^{3+}$ and $Fe^{2+}$ in the completely discharged state. In some embodiments the electrolyte comprises an acidic solution comprising $Fe^{2+}$, $Fe^{3+}$ and $Cr^{3+}$. In further or additional embodiments the electrolyte comprises an acidic solution comprising $Cr^{3+}$ and $Fe^{3+}$ in the completely charged state and $Cr^{3+}$ and $Fe^{2+}$ in the completely discharged state. In some embodiments the spectrophotometer comprises at least one light emitter and at least one light receiver. In further or additional embodiments the light emitters of the spectrophotometer are Light Emitting Diodes (LEDs). In further or additional embodiments the light emitters of the spectrophotometer emit light as photometric beams with spectral bandwidths less than about 50 nm at FWHM (Full Width at Half Maximum). In further or additional embodiments the spectrophotometer comprises two light emitters. In further or additional embodiments the spectrophotometer comprises two light emitters, wherein one light emitter is for anolyte photometry and one light emitter is for catholyte photometry. In further or additional embodiments the anolyte light emitter emits light of wavelength from about 700 nm to about 1000 nm and the catholyte light emitter emits light of wavelength from about 800 nm to about 1000 nm. In some embodiments the light receiver of the spectrophotometer further comprises at least one filter. In further or additional embodiments the filter filters incoming photometric beams to produce incoming photometric beams with spectral bandwidths less than about 50 nm at FWHM (Full Width at Half Maximum). In some embodiments the electrolyte state of charge measuring systems further comprises at least one transparent tube. In further or additional embodiments the at least one transparent tube intercepts at least one of the photometric beams. In further or additional embodiments at least one electrolyte flows through at least one of the transparent tubes. In further or additional embodiments the at least one transparent tube is curved. In further or additional embodiments the curvature of at least one of the transparent tubes imparts a lensing effect on at least one of the photometric beams. In further or additional embodiments said lensing effect increases the photometric density of light falling on the detector, resulting in an increase in the signal-to-noise ratio of the photometric measurement. In some embodiments the means for correlating the optical absorption spectra of the at least one electrolyte with its state of charge uses analog circuits, application specific integrated circuits (ASICs), mixed signal circuits, algorithms, look up tables, correlation tables, correlation graphs or any combination thereof.

Further described herein are methods for determining the state of charge of an electrolyte, wherein the electrolyte exhibits different optical absorption spectra in oxidized and reduced forms. In some embodiments, the methods comprise the following steps:

a) providing reference optical absorption spectrum of said electrolyte in pure fully oxidized and pure fully reduced forms;

b) providing a test sample of said electrolyte, of which the state of charge is to be determined;

c) measuring the optical absorption spectrum of said test sample of electrolyte;

d) correlating the optical absorption spectrum of said test sample with the optical absorption spectra of said pure oxidized and reduced samples to provide the relative absorptivity of the test sample; and e) determining the state of charge of the electrolyte from the relative absorptivity of the test sample. In further or additional embodiments the step of providing reference optical absorption spectrum of the electrolyte in pure fully oxidized and pure fully reduced forms comprises the steps of i) providing a pure sample of said electrolyte in fully oxidized form;

ii) measuring the optical absorption spectrum of said pure oxidized electrolyte;

iii) providing a pure sample of said electrolyte in fully reduced form; and iv) measuring the optical absorption spectrum of said pure reduced electrolyte.

In further or additional embodiments the step of determining the state of charge of the electrolyte from the relative absorptivity of the test sample may involve the use of analog circuits, application specific integrated circuits (ASICs), mixed signal circuits, algorithms, look up tables, correlation tables, correlation graphs or any combination thereof. In some embodiments, the electrolyte comprises an acidic solution. In further or additional embodiments, the acidic electrolyte solution comprises hydrochloric acid, hydrobromic acid or a mixture thereof. In further or additional embodiments, the acidic electrolyte solution further comprises aqueous metal chloride salts. In further or additional embodiments the absorption wavelength of the electrolyte is between about 400 nm and 700 nm, between about 730 nm and 1100 nm or is greater than about 750 nm. In some embodiments the concentration of the electrolyte solution is at least 0.1M. In further or additional embodiments the concentration of the electrolyte solution is at least 0.2M. In further or additional embodiments the concentration of the electrolyte solution is at least 0.5M. In further or additional embodiments the concentration of the electrolyte solution is from about 0.1M to about 15M. In further or additional embodiments the concentration of the electrolyte solution is from about 0.2M to about 10M. In further or additional embodiments the concentration of the electrolyte solution is from about 0.5M to about 8M. In some embodiments the electrolyte comprises an acidic solution comprising $Cr^{2+}$, $Cr^{3+}$ and $Fe^{2+}$. In further or additional embodiments the electrolyte comprises an acidic solution comprising $Cr^{2+}$ and $Fe^{2+}$ in the completely charged state and $Cr^{3+}$ and $Fe^{2+}$ in the completely discharged state. In some embodiments the electrolyte comprises an acidic solution comprising $Fe^{2+}$, $Fe^{3+}$ and $Cr^{3+}$. In further or additional embodiments the electrolyte comprises an acidic solution comprising $Cr^{3+}$ and $Fe^{3+}$ in the completely charged state and $Cr^{3+}$ and $Fe^{2+}$ in the completely discharged state. In some embodiments the optical absorption spectrum of the test sample of electrolyte is measured using a spectrophotometer. In further or additional embodiments the spectrophotometer comprises at least one light emitter and at least one light receiver. In further or additional embodiments the light emitters of the spectrophotometer are Light Emitting Diodes (LEDs). In further or additional embodiments the light emitters of the spectrophotometer emit light as photometric beams with spectral bandwidths less than about 50 nm at FWHM (Full Width at Half Maximum). In further or additional embodiments the spectrophotometer comprises two light emitters. In further or additional embodiments the light emitter emits light of wavelength from about 700 nm to about 1000 nm. In further or additional embodiments the light emitter emits light of wavelength from about 800 nm to about 1000 nm. In some embodiments the light receiver of the spectrophotometer further comprises at least one filter. In further or additional embodiments the filter filters incoming photometric beams to produce incoming photometric beams with spectral bandwidths less than about 50 nm at FWHM (Full Width at Half Maximum).

Also described are methods for determining if a redox system is out of electrolyte charge balance and, if the redox system is found to be out of charge balance, methods for restoring the electrolyte charge balance of the redox system.

In some embodiments, these methods comprise the following steps:

a) providing a redox system comprising a first electrolyte that exhibits a first optical absorption spectrum and a second electrolyte that exhibits a second optical absorption spectrum;

b) measuring the optical absorption spectra of said electrolytes;

c) determining the state of charge of said electrolytes from the absorption spectra;

d) determining if the state of charge of either said first and/or said second electrolyte falls below predetermined threshold limits; and e) directing electrolyte flow through a rebalance battery if the state of charge of either said first and/or said second electrolyte falls below said predetermined threshold limits.

In further or additional embodiments the step of determining the state of charge of said electrolytes from the absorption spectra may involve the use of analog circuits, application specific integrated circuits (ASICs), mixed signal circuits, algorithms, look up tables, correlation tables, correlation graphs or any combination thereof. In further or additional embodiments the step of determining if the state of charge of either said first and/or said second electrolyte falls below predetermined threshold limits may involve the use of analog circuits, application specific integrated circuits (ASICs), mixed signal circuits, algorithms, look up tables, correlation tables, correlation graphs or any combination thereof. In some embodiments, the first electrolyte comprises an acidic solution. In further or additional embodiments, the acidic electrolyte solution comprises hydrochloric acid, hydrobromic acid or a mixture thereof. In further or additional embodiments, the acidic electrolyte solution further comprises aqueous metal chloride salts. In further or additional embodiments the absorption wavelength of the first electrolyte is greater than about 750 nm. In further or additional embodiments, the second electrolyte comprises an acidic solution. In further or additional embodiments, the acidic electrolyte solution comprises hydrochloric acid, hydrobromic acid or a mixture thereof. In further or additional embodiments, the acidic electrolyte solution further comprises aqueous metal chloride salts. In further or additional embodiments the absorption wavelength of the second electrolyte is between about 400 nm and 700 nm or between about 730 nm and 1100 nm. In some embodiments the concentrations of the first electrolyte and the second electrolyte solutions are different. In further or additional embodiments the concentrations of the first electrolyte and the second electrolyte solutions are substantially the same. In further or additional embodiments the concentrations of the first electrolyte and the second electrolyte solutions are the same. In yet other embodiments the concentrations of the first electrolyte and the second electrolyte solutions are at least 0.1M. In further or additional embodiments the concentrations of the first electrolyte and the second electrolyte solutions are at least 0.2M. In further or additional embodiments the concentrations of the first electrolyte and the second electrolyte solutions are at least 0.5M. In further or additional embodiments the concentrations of the first electrolyte and the second electrolyte solutions are from about 0.1M to about 15M. In further or additional embodiments the concentrations of at the concentrations of the first electrolyte and the second electrolyte solutions are from about 0.2M to about 10M. In further or additional embodiments the concentrations of the first electrolyte and the second electrolyte solutions are from about 0.5M to about 8M. In some embodiments the first electrolyte is an anolyte. In other embodiments the first electrolyte is a catholyte. In some embodiments, the second electrolyte is an anolyte. In other embodiments the second electrolyte is a catholyte. In some embodiments the anolyte comprises an acidic solution comprising $Cr^{2+}$, Cr and $Fe^{2+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state. In some embodiments the catholyte comprises an acidic solution comprising $Fe^{2+}$, $Fe^{3+}$ and $Cr^{3+}$. In further or additional embodiments the catholyte comprises an acidic solution comprising $Cr^{3+}$ and $Fe^{3+}$ in the completely charged state and $Cr^{3+}$ and $Fe^{2+}$ in the completely discharged state. In some embodiments the anolyte comprises an acidic solution comprising $Cr^{2+}$, $Cr^{3+}$ and $Fe^{2+}$ and the catholyte comprises an acidic solution comprising $Fe^{2+}$, $Fe^{3+}$ and $Cr^{3+}$. In further or additional embodiments the anolyte comprises an acidic solution comprising $Cr^{2+}$ and $Fe^{2+}$ in the completely charged state and $Cr^{3+}$ and $Fe^{2+}$ in the completely discharged state and the catholyte comprises an acidic solution comprising $Cr^{3+}$ and $Fe^{3+}$ in the completely charged state and $Cr^{3+}$ and $Fe^{2+}$ in the completely discharged state. In some embodiments the optical absorption spectrum of the electrolytes is measured using a spectrophotometer. In further or additional embodiments the spectrophotometer comprises at least one light emitter and at least one light receiver. In further or additional embodiments the light emitters of the spectrophotometer are Light Emitting Diodes (LEDs). In further or additional embodiments the light emitters of the spectrophotometer emit light as photometric beams with spectral bandwidths less than about 50 nm at FWHM (Full Width at Half Maximum). In further or additional embodiments the spectrophotometer comprises two light emitters. In further or additional embodiments the spectrophotometer comprises two light emitters, wherein one light emitter is for anolyte photometry and one light emitter is for catholyte photometry. In further or additional embodiments the anolyte light emitter emits light of wavelength from about 700 nm to about 1000 nm and the catholyte light emitter emits light of wavelength from about 800 nm to about 1000 nm. In some embodiments the light receiver of the spectrophotometer further comprises at least one filter. In further or additional embodiments the filter filters incoming photometric beams to produce incoming photometric beams with spectral bandwidths less than about 50 nm at FWHM (Full Width at Half Maximum). In some embodiments the redox system further comprises at least one transparent tube. In further or additional embodiments the redox system further comprises two transparent tubes. In further or additional embodiments the at least one transparent tube intercepts at least one of the photometric beams. In further or additional embodiments the first electrolyte flows through one transparent tube. In further or additional embodiments the second electrolyte flows through one transparent tube. In further or additional embodiments the redox system further comprises two transparent tubes wherein the first electrolyte flows through one transparent tube and the second electrolyte flows the second transparent tube. In further or additional embodiments the at least one transparent tube is curved. In further or additional embodiments the curvature of at least one of the transparent tubes imparts a lensing effect on at least one of the photometric beams. In further or additional embodiments said lensing effect increases the photometric density of light falling on the detector, resulting in an increase in the signal-to-noise ratio of the photometric measurement.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings. The drawings included herewith are incorporated in and form a part of this specification. It should be understood that the drawings referred to in this description are not drawn to scale unless specifically noted as such.

DETAILED DESCRIPTION OF THE INVENTION

Figure 1:
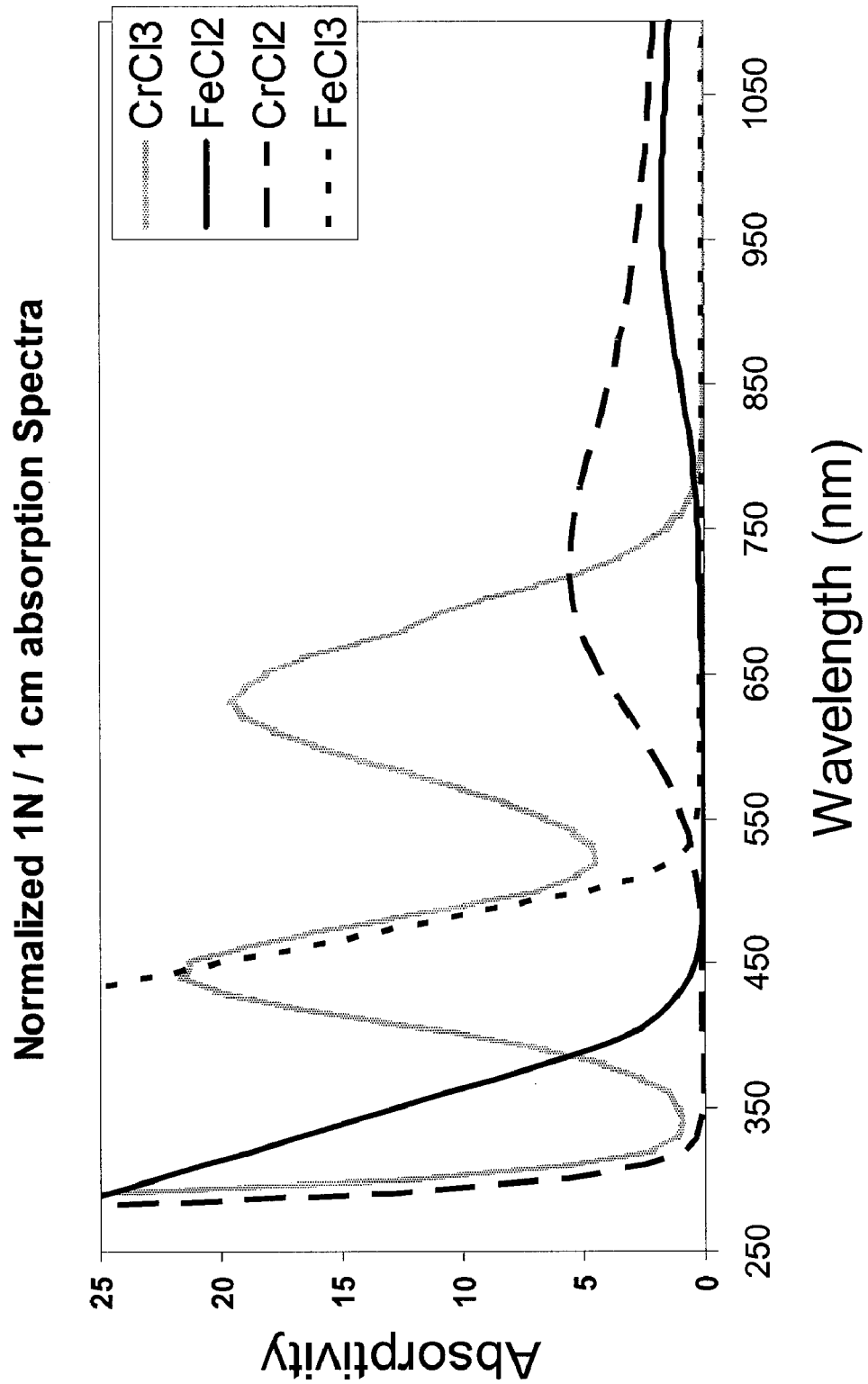
FIG. 1 represents the absorption spectra (a graphical plot of absorptivity versus wavelength) of $FeCl_3$, $CrCl_3$, $FeCl_2$, and $CrCl_2$, in accordance with one embodiment of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unlike other power sources (e.g. natural gas), electricity must be used as it is generated, and thus fluctuating demand is difficult to accommodate without either periodically cutting supplies, or having expensive excess capacity. Reasons for fluctuating demand are many and varied and may include any of the following:

Seasonal, whereby during cold, dark winters additional electric heating and lighting is required, while hot weather boosts demand for air conditioning Weekly, in which most offices and industry closes at the weekend, lowering demand Daily, such as peaks that occur as families arrive home from work/school or air conditioners working hard in early summer afternoons Hourly, for example power spikes during commercial breaks on TV, when consumers turn on additional lights, heaters, appliances, etc Transient, due to fluctuations in an individual's actions, differences in power transmission efficiency and other small factors.

Possible methods for dealing with fluctuating demand include running power plants below normal output, with the ability to rapidly increase production, or bringing online additional dormant power plants to boost output. However, these methods are costly, as expensive generating equipment is frequently left unused, and because plants running below maximum output are often less efficient.

Thus, storage of electrical energy is a major concern, and many electrical energy storage methods have been examined to address this problem. These include electrical (such as, but not limited to capacitors and superconducting magnetic energy storage), electrochemical (such as, but not limited to batteries, flow batteries and fuel cells), mechanical (such as, but not limited to compressed air, flywheels, hydraulic accumulators, hydroelectric and springs), potential (gravity, such as, but not limited to hydroelectric) and thermal (such as, but not limited to molten salts, cryogenic liquids, seasonal thermal storage and solar ponds). Though a number of technologies have been investigated and developed, thus far, widely available, highly efficient, affordable solutions to the problem of mass electrical energy storage remain to be developed. One method that begins to address these needs involves the use of redox flow batteries.

Redox flow batteries can be used for storage of electrical energy (for example, though not limited to storage of cheap night-time electricity to provide electricity during peak demand or for storage of green energy, i.e. energy generated from renewable sources such as wind, solar, wave, etc.) or to provide an uninterruptible power supply (UPS) where the energy source is activated should the main power fail. UPS is important as many devices that operate on electricity are adversely affected by the sudden removal of their power supply, and while backup generators address this problem, they are expensive. Efficient methods of power storage could provide for devices to have a built-in backup for power cuts or sudden power failures, and also reduce the impact of a failure in a generating station. Other instances where uninterruptible power supplies are of importance include, but are not limited to buildings where uninterrupted power is critical, such as hospitals or for providing an uninterruptible power supply to for example developing countries, many of which do not have reliable electrical power sources and the power supply is intermittent. Another possible use is in electric vehicles as they can be rapidly "recharged" by replacing the electrolyte(s) (which would require subsequent recharging elsewhere).

As used in the present specification, the following words and phrases are generally intended to have the meanings as set forth below, except to the extent that the context in which they are used indicates otherwise.

The term "energy storage" as used herein refers to the storing of some form of energy that can be drawn upon at a later time.

The term "electrical energy storage" as used herein refers to the storing of electrical energy that can be drawn upon at a later time to power electrical appliances.

The term "electrochemical energy storage" as used herein refers to the storing of electrical energy in a chemical form through an electrochemical reaction that can be drawn upon at a later time to power electrical appliances.

The term "electrical energy storage system" as used herein refers to a device capable of storing of electrical energy that can be drawn upon at a later time to power electrical appliances.

The terms "cells", "galvanic cells", "voltaic cells" and the like as used herein refer to two half cells connected in series by a conductive electrolyte.

The term "electrolyte" as used herein refers to an electrically conductive solution comprising ionic species.

The term "anolyte" as used herein refers to an electrolyte having a net negative electrode potential ($E_o$) compared to a Standard Hydrogen Electrode (SHE) during discharge of the system.

The term "catholyte" as used herein refers to an electrolyte having a net positive electrode potential ($E_o$) compared to a Standard Hydrogen Electrode (SHE) during discharge of the system.

The term "acidic solution" as used herein refers to a solution of pH 7 or below. The acidic solutions described herein may further comprise at least one electrolyte.

The term "photometry" as used herein refers to measuring the various properties of visible light.

The term "spectrophotometry" as used herein refers to measuring the optical absorption spectra of solids, liquids and/or solutions.

The term "spectrophotometer" as used herein refers to a device used to measure the amount of light that a sample material absorbs as a function of wavelength. The instrument operates by generating a beam of light (consisting of a stream of photons, referred to as a photometric beam), from a light source, that passes through a sample and then measuring the intensity of the light reaching a light detector.

The term "optical absorption spectra" as used herein refers to a graphical plot of absorbance vs. wavelength for a given substance, as measured by a spectrophotometer.

The terms "absorption wavelength" and "$\lambda_{max}$" as used herein refer to the wavelength at which the absorbance of any given substance is the greatest.

The terms "light emitting diode" and "LED" as used herein refer to a semiconductor device that emits narrow-spectrum light.

The term "different optical absorption spectra in reduced and oxidized forms" as used herein refers to solutions of electrolytes wherein a solution of an electrolyte in a reduced state has a different optical absorption spectra, as described herein, to a solution of the same electrolyte in an oxidized state. i.e. there is at least one wavelength where the two states have absorptivities differing by more than 5%.

The term "lensing effect" as used herein refers to the optical intensification of a light beam which increases the photometric density of light falling on the detector, resulting in an increase in the signal-to-noise ratio of the photometric measurement.

The term "electrolyte rebalancing" as used herein refers to a mechanism that reduces or oxidizes either the anolyte or the catholyte or both of a redox system, when a charge imbalance between the anolyte and catholyte is detected. In some embodiments this may be achieved by directing electrolyte flow through a rebalance cell.

Many redox energy storage systems comprise electrolyte solutions that are highly colored, and thus display strong absorption bands in their optical absorption spectra. Additionally, the colors of the electrolytes in their oxidized and reduced states are different and discernable with a spectrophotometer. By measuring the optical absorption of the electrolyte at any given time during the operation of the redox flow battery, one may determine the concentration of the species using Beer's law:

$$I = I_o e^{-act} (\text{or } I = I_o \exp(-(act)))$$

where $I_o$ is the intensity of light emitted at a given wavelength;

I is the intensity of light transmitted through the electrolyte solution at the same wavelength;

a is the molar absorptivity of the electrolyte at the same wavelength ($L\ mol^{-1}\ cm^-$);

c is the electrolyte species concentration ($mol\ L^{-1}$); and t is the electrolyte sample path length (cm).

Assumptions are made in using this equation, such as that the medium is optically linear and that there is no fluorescence or phosphorescence in the medium or intervening system. If more than one colored electrolyte is present in the system, then the Composite Beer's law appears as:

$$I = I_o * \exp-(a_1 * c_1 + a_2 * c_2 + \ldots + a_n * c_n)t, \text{ where}$$

$a_i$ is the molar absorptivity of electrolyte i at a given wavelength, and $c_i$ is electrolyte i concentration ($mol\ L^{-1}$).

Thus, in an ideal situation (i.e. no cross-contamination of reactants) the concentration of the electrolytes in the redox cell can be easily calculated by measuring the absorptivity of the electrolyte.

Using an Fe/Cr system as an ideal, non-limiting example the catholyte is a solution comprising a mixture of $Fe^{2+}$ and $Fe^{3+}$, whereas the anolyte is a solution comprising a mixture of $Cr^{3+}$ and $Cr^{2+}$. The absorption spectra of these salts (as chlorides in 1N hydrochloric acid) are shown in FIG. 1, as measured with a standard infrared/visible spectrophotometer. It should be noted that the individual ions of the salts may not be present as discrete entities, but may form complexes or aggregates in aqueous solution. As such, the resultant spectrum is a convolution of spectra from all such forms.

In order to be able to determine the state of charge of the system, the individual spectrum of each electrolyte, in both the oxidized and reduced forms, should be discernable. Using the Fe/Cr system demonstrated in FIG. 1 as a non-limiting example, two regions of the absorption spectra can be seen where the spectrum of the four specifies are discernable. The first occurs at the near-UV wavelengths, around 440 nm, where there is significant spectral differentiation between each of these salts. $CrCl_2$ shows essentially no absorbance at 440 nm; $FeCl_2$ shows very little, with an absorptivity of 2-3; $CrCl_3$ shows significant absorbance of 19 and $FeCl_3$ having a very large absorptivity. The second occurs at the visible/near-IR wavelengths, around 700 nm or more. $CrCl_2$ shows highest absorbance around ~4; $FeCl_2$ has an absorptivity of 3; and $CrCl_3$ and $FeCl_3$ have absorbances of >0.

In selecting which region of the spectrum should be used to determine the state of charge of the redox system, various factors should be considered. For example, the very high absorptivities at the lower wavelengths can make the photometric measurements quite difficult, (although this could be overcome by using very thin electrolyte sample paths).

The absorptivities at higher wavelengths tend to be smaller (less than or about 5), making the measurements more straight forward. Additionally, the light sources and filters required for near-UV wavelengths are expensive, while those for longer wavelengths are easy to obtain (for example, LEDs are commercially available at such wavelengths), and reasonably small.

It should be noted that the system would also work at infrared and far infrared wavelengths (>1000 nm), although the cost of light emitters, filters and detectors for these wavelengths is also greater.

Thus, the detection systems described herein can be used at wavelengths in the infrared/far infrared range (>~700 nm), the near-IR range (630-700 nm), the visible range (~440-630 nm), the near UV range (~380-440 nm) or any combination thereof. In some embodiments of the invention, an infrared/far infrared detection system is used. In other embodiments of the invention, a visible/near-IR detection system is used. In yet other embodiments, a visible detection system is used. In further embodiments, a near-UV detection system is used. In yet further embodiments, a combination of detection systems are used.

It should be noted that the diffusion equilibrium point between anolyte and catholyte may not be at an exact 1:1 ratio. This arises from the fact that not all ion exchange membranes will affect the same cross-diffusion rates for the various electrolyte species, and that different electrolyte species will diffuse at different rates. However, in such cases, the equilibrium point can easily be established empirically by experimentation and the system can then be operated employing the optimal electrolyte ratios.

As described above, a redox flow battery in which the anolyte and catholyte are pre-mixed overcomes the problem of cross-diffusion of species, helping to maintain charge balance and the net system capacity. The Fe/Cr redox flow battery described above will be used as an illustrative non-limiting example. It should be understood that the methods of determining the state of charge of a redox system described herein will be equally as applicable to separate (non-mixed) reactant redox systems as to mixed reactant systems. Thus, assuming an ideal ion exchange membrane, the mixed reactant Fe/Cr redox flow battery would comprise premixed Fe and Cr acidic solutions in the molar ratios indicated in the table below:

| | State of Charge | | | | |
|---|---|---|---|---|---|
| | Fully Charged | Partially Charged | 50/50 | Partially Discharged | Fully Discharged |
| Catholyte species | | | | | |
| $CrCl_3$ | 1 | 1 | 1 | 1 | 1 |
| $FeCl_3$ | 1 | 0.5-1 | 0.5 | 0-0.5 | 0 |
| $FeCl_2$ | 0 | 0-0.5 | 0.5 | 0.5-1 | 1 |
| Anolyte species | | | | | |
| $FeCl_2$ | 1 | 1 | 1 | 1 | 1 |
| $CrCl_2$ | 1 | 0.5-1 | 0.5 | 0-0.5 | 0 |
| $CrCl_3$ | 0 | 0-0.5 | 0.5 | 0.5-1 | 1 |

Figure 2:
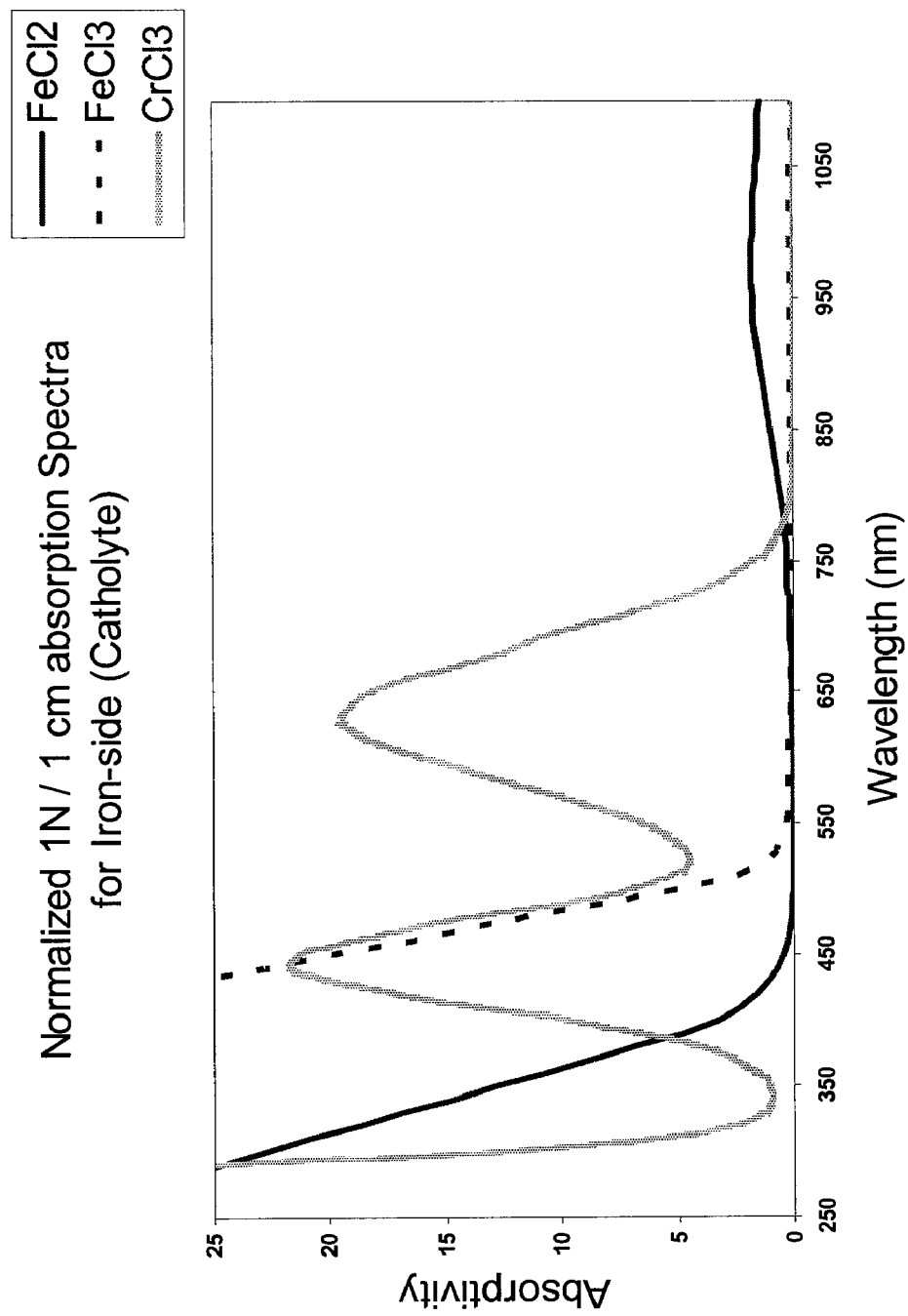
FIG. 2 represents the absorption spectra (a graphical plot of absorptivity versus wavelength) of the individual electrolyte species ($FeCl_2$, $FeCl_3$ and $CrCl_3$) present on the iron side (Catholyte) of a mixed reactant half cell, in accordance with one embodiment of the present invention.

Thus, the completely charged catholyte comprises 50% $CrCl_3$ and 50% $FeCl_3$ in molar proportions, while the completely discharged catholyte comprises 50% $CrCl_3$ and 50% $FeCl_2$ in molar proportions. At any given state of charge between these two extremes, the catholyte would consist of 50% $CrCl_3$ and a mixture of $FeCl_2$ and $FeCl_3$. The absorption spectra of these three separate solutions (1M in 1N HCl) are shown in FIG. 2, (sample path=1 cm).

Figure 3:
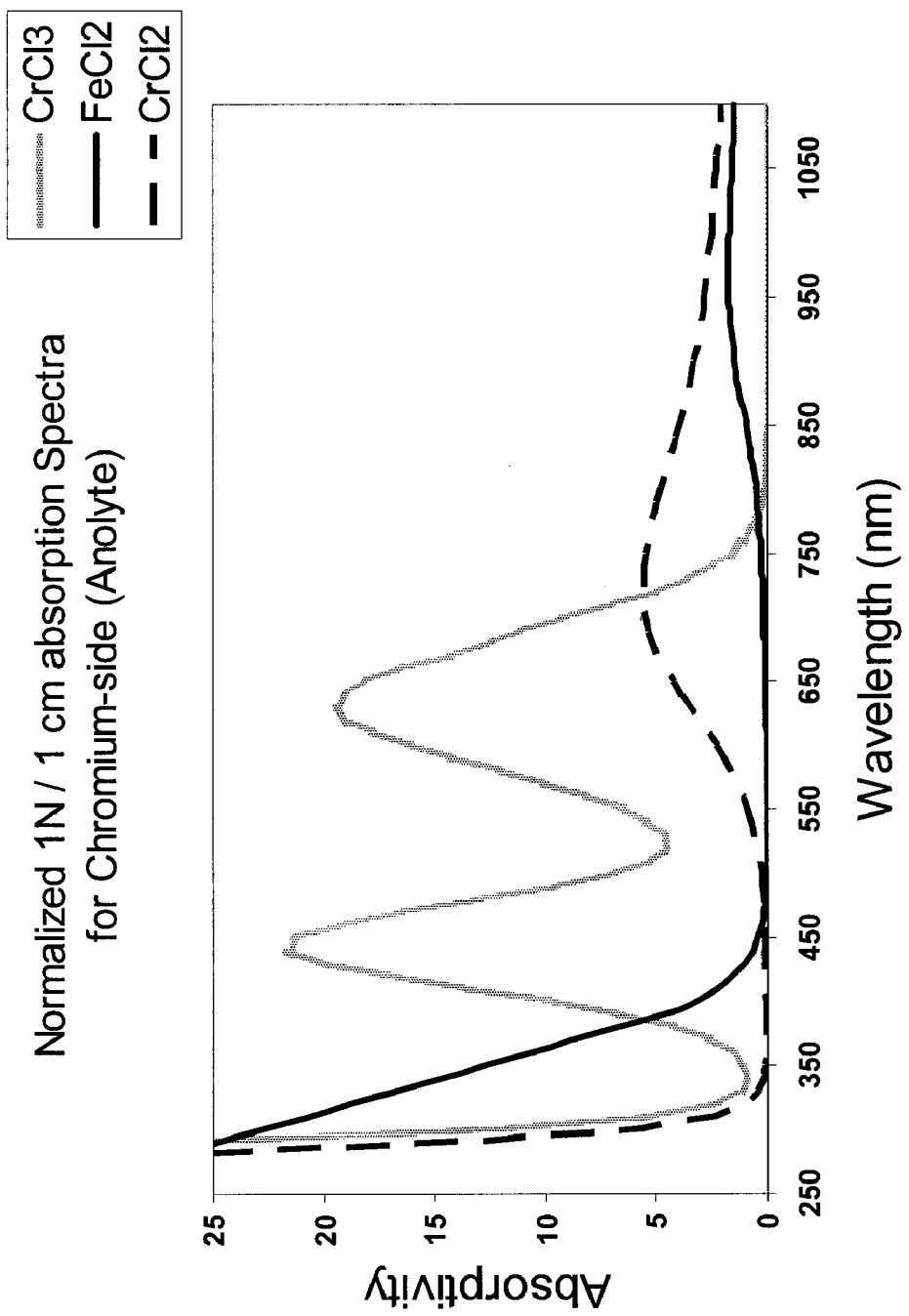
FIG. 3 represents the absorption spectra (a graphical plot of absorptivity versus wavelength) of the individual electrolyte species ($CrCl_2$, $CrCl_3$ and $FeCl_2$) present on the chromium side (Anolyte) of a mixed reactant half cell, in accordance with one embodiment of the present invention.

Thus, the completely charged anolyte comprises 50% $FeCl_2$ and 50% $CrCl_2$ in molar proportions, while the completely discharged anolyte comprises 50% $FeCl_2$ and 50% $CrCl_3$ in molar proportions. At any given state of charge between these two extremes, the anolyte would consist of 50% $FeCl_2$ and a mixture of $CrCl_2$ and $CrCl_3$. The absorption spectra of these three separate solutions (1M in 1N HCl) are shown in FIG. 3, (sample path=1 cm).

The Composite Beer's Law described earlier is applied for the 3 components on each side and used to calculate the resulting spectra for different states of charge for anolyte and catholyte.

Figure 4:
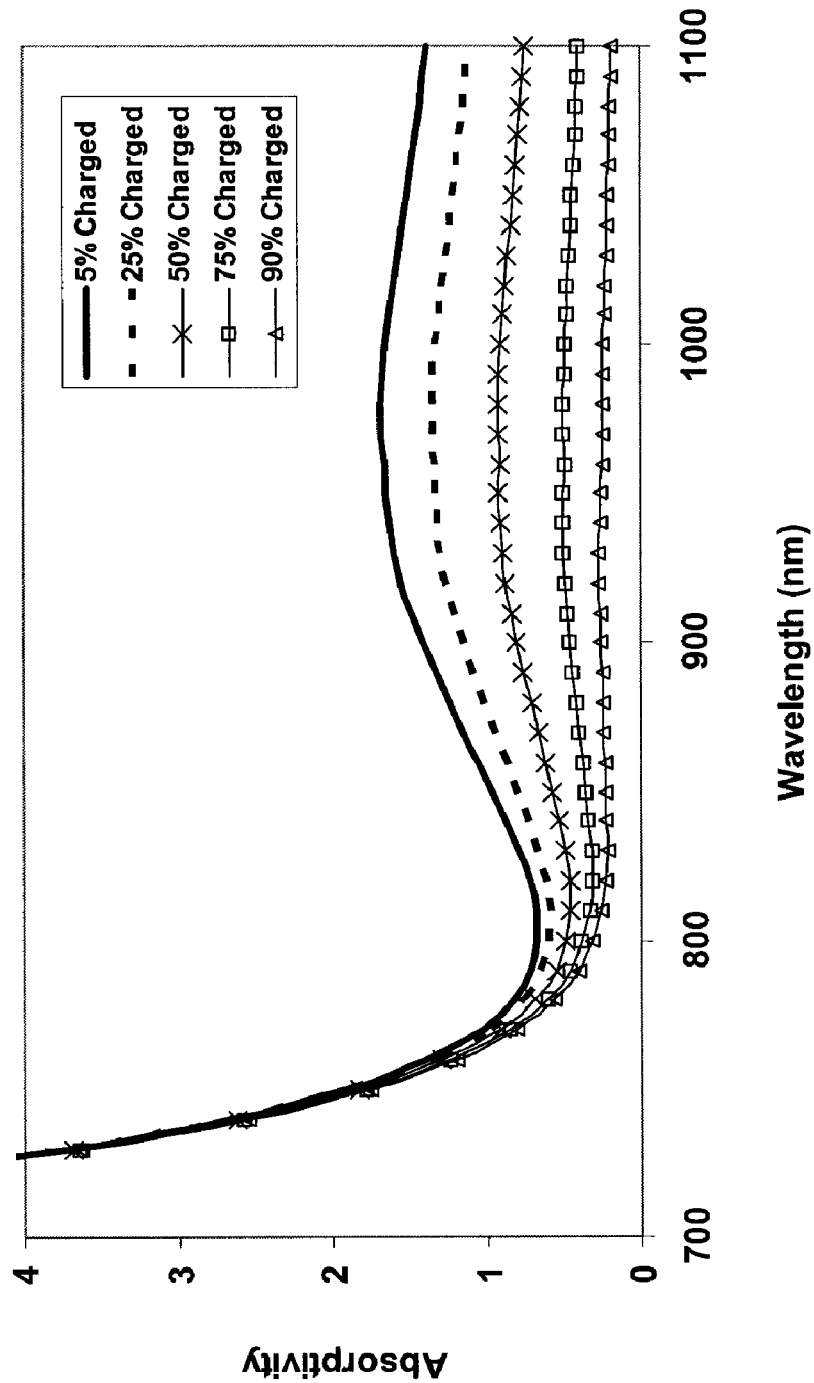
FIG. 4 represents the absorption spectra (a graphical plot of absorptivity versus wavelength) of the iron side (Catholyte) of a mixed reactant half cell, at different states of charge/discharge (5% charged, 25% charged, 50% charged, 75% charged and 95% charged), in accordance with one embodiment of the present invention.

Absorptivity plots for the catholyte for states of charge of 5% (almost fully discharged), 25%, 50%, 75% and 90% (almost fully charged) are shown in FIG. 4. It can be observed that the spectra are well distinguished in absorptivity at wavelengths longer than about 800 nm. In this range all the absorptivities are below about 2, thus easing the dynamic range of spectrometry.

Figure 5:
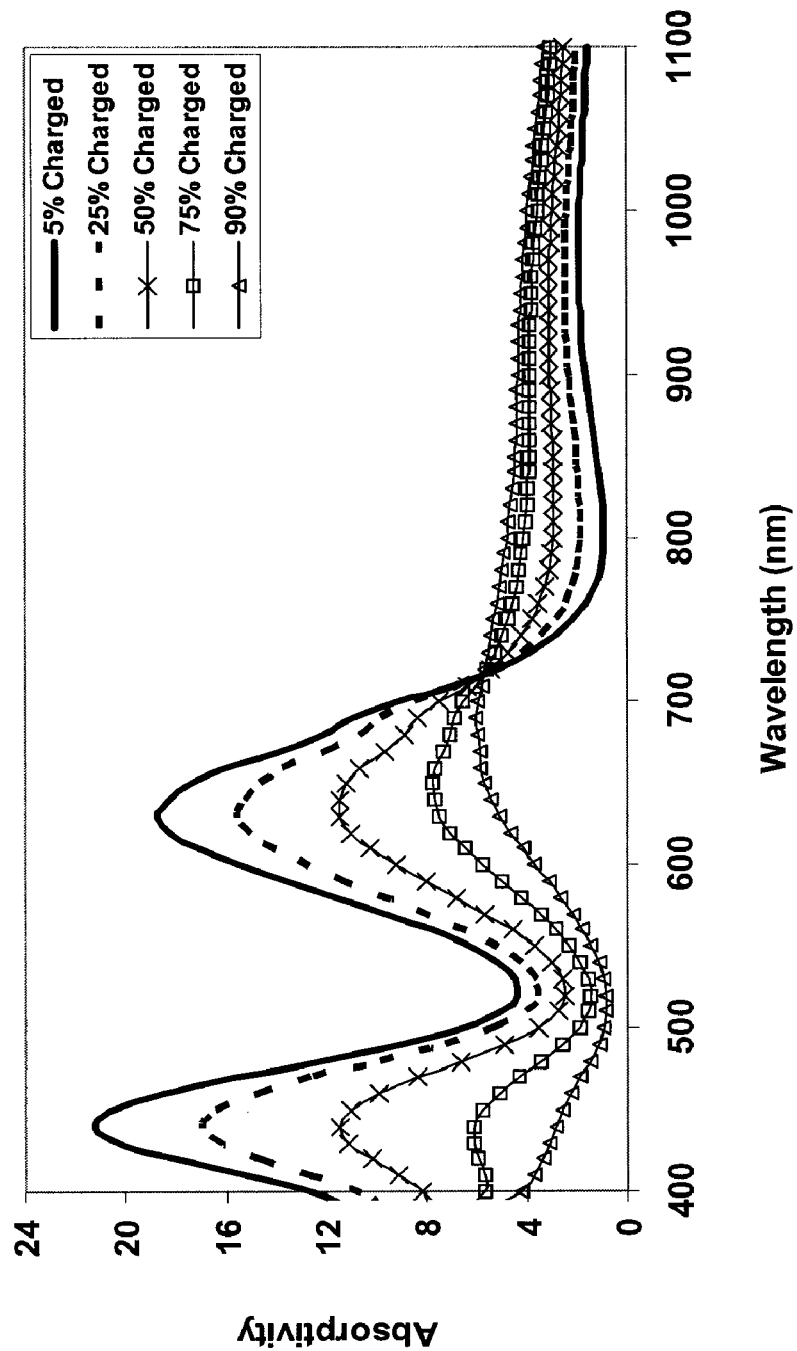
FIG. 5 represents the absorption spectra (a graphical plot of absorptivity versus wavelength) of the chromium side (Anolyte) of a mixed reactant half cell, at different states of charge/discharge (5% charged, 25% charged, 50% charged, 75% charged and 95% charged), in accordance with one embodiment of the present invention.

Absorptivity plots for the anolyte for states of charge of 5% (almost fully discharged), 25%, 50%, 75% and 90% (almost fully charged) are shown in FIG. 5. It can be observed that the spectra are well distinguished in absorptivity at all wavelengths in the UV, Visible and near-IR (400 nm-1100 nm) ranges, other than a narrow inflection point at about 720 nm. Therefore practical devices based on this non-limiting example of the Fe/Cr system, could be built in this entire range, excepting round 720 nm.

In some embodiments, the absorption vs. wavelength data for different states of charge are calibrated against pure electrolyte solutions. In other embodiments, the absorption vs. wavelength data for different states of charge are calibrated during the initial cell cycles (when any charge imbalance is insignificant).

As the dynamic range of photonics measurements are easier to handle when the range of absorptivities are smaller (below for example about 4), wavelengths may be selected corresponding to regions of lower absorptivities. Thus for the exemplary Fe/Cr system, higher wavelengths would be preferred, such as for example above about 750 nm.

Using the calibrated absorption vs. wavelength data for different states of charge, the state of charge of the electrolytes at any time during the operation of the device can be determined.

The redox flow cells described herein, will comprise at least one electrolyte, (and any respective storage vessels, tubing, valves, etc), at least one ion exchange membrane, spectrophotometry apparatus for use in measuring the state of charge of at least one of the electrolytes and a rebalance mechanism. Various electrolytes, (and their respective storage vessels, tubing, valves, etc), and ion exchange membranes have been well documented and are well known to those of skill in the art.

The redox flow cells described herein may comprise two electrolytes, an anolyte and a catholyte. Substances that can act as electrolytes, anolytes and catholytes are well known to those of skill in the art. For the redox flow cells described herein, the concentrations of the electrolytes can vary widely. Clearly, the higher the electrolyte concentration, the greater the capacity of the system. However, at higher concentrations, the measurement of the optical absorption spectra may become problematic. One way to overcome such problems, would be to use optical cells that have reduced pathlengths (refer to Beer's Law above, which relates the intensity of light transmitted through the electrolyte solution to the electrolyte sample path length). For example, typical sample cell pathlengths are 1 cm. By reducing the sample cell pathlength to 1 mm, the concentration of the sample can be increased correspondingly with no effect on the quality of the optical absorption spectra. Further reductions in sample cell pathlength will allow for further increases in concentration. Obviously the sample cell pathlength cannot become infinitely small, and thus the electrolyte concentration cannot be infinitely high.

The electrolytes described herein may comprise acidic solutions. They may further comprise additional components, such as solubility enhancers, compounds useful for helping to maintain the electrolyte charge balance and the like. Addition of certain metal halide salts may help these factors. For example, addition of metal chloride salts aids in solubilizing some of the other components of the electrolyte solution and/or once dissolved, in maintaining those components in solution.

Figure 6A:
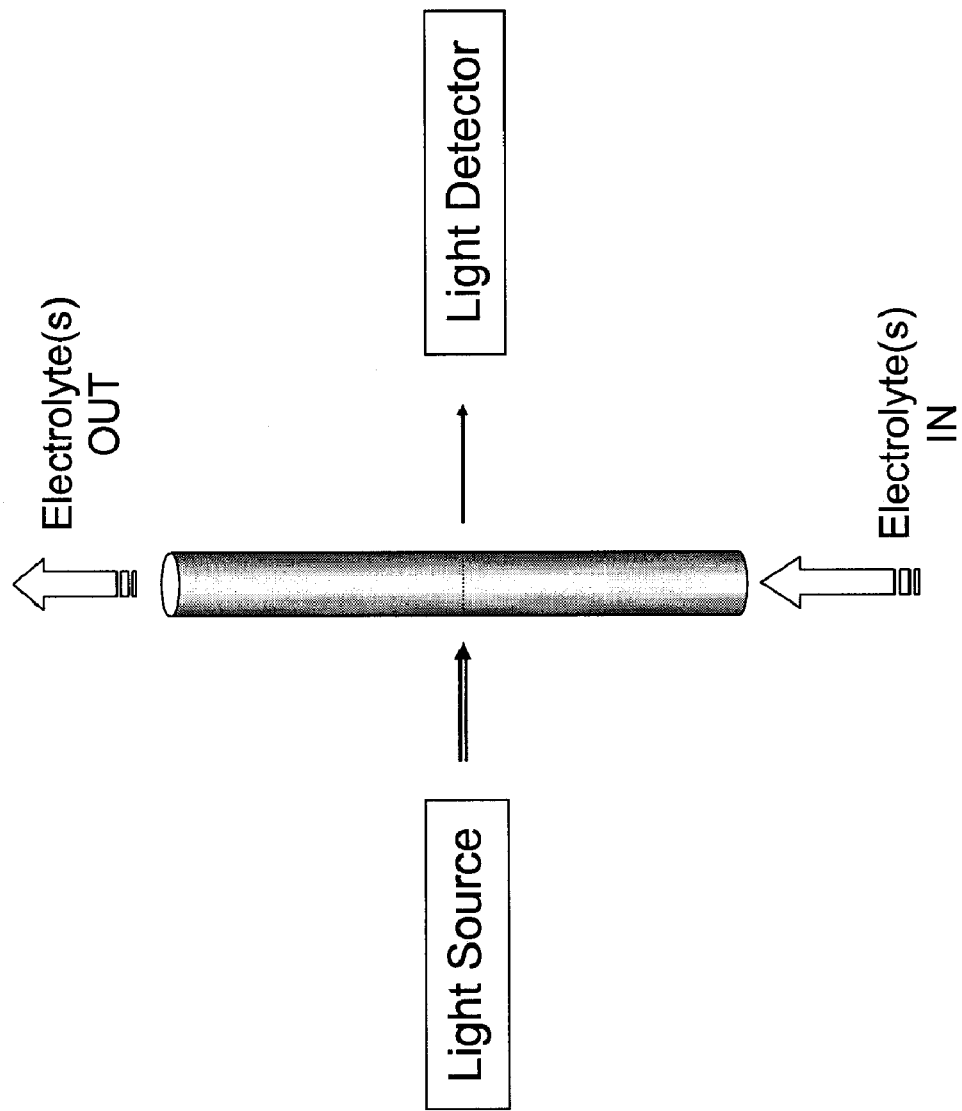
FIG. 6A represents a diagram of a spectrophotometer for use in measuring the charge state of at least one electrolyte, in accordance with one embodiment of the present invention.

FIG. 6A depicts a non-limiting example of the spectrophotometry apparatus as described herein for use in measuring the state of charge of at least one electrolyte. A light source generates a photonic beam, which crosses the path of at least one electrolyte and the incident light is detected by a light detector.

Figure 6B:
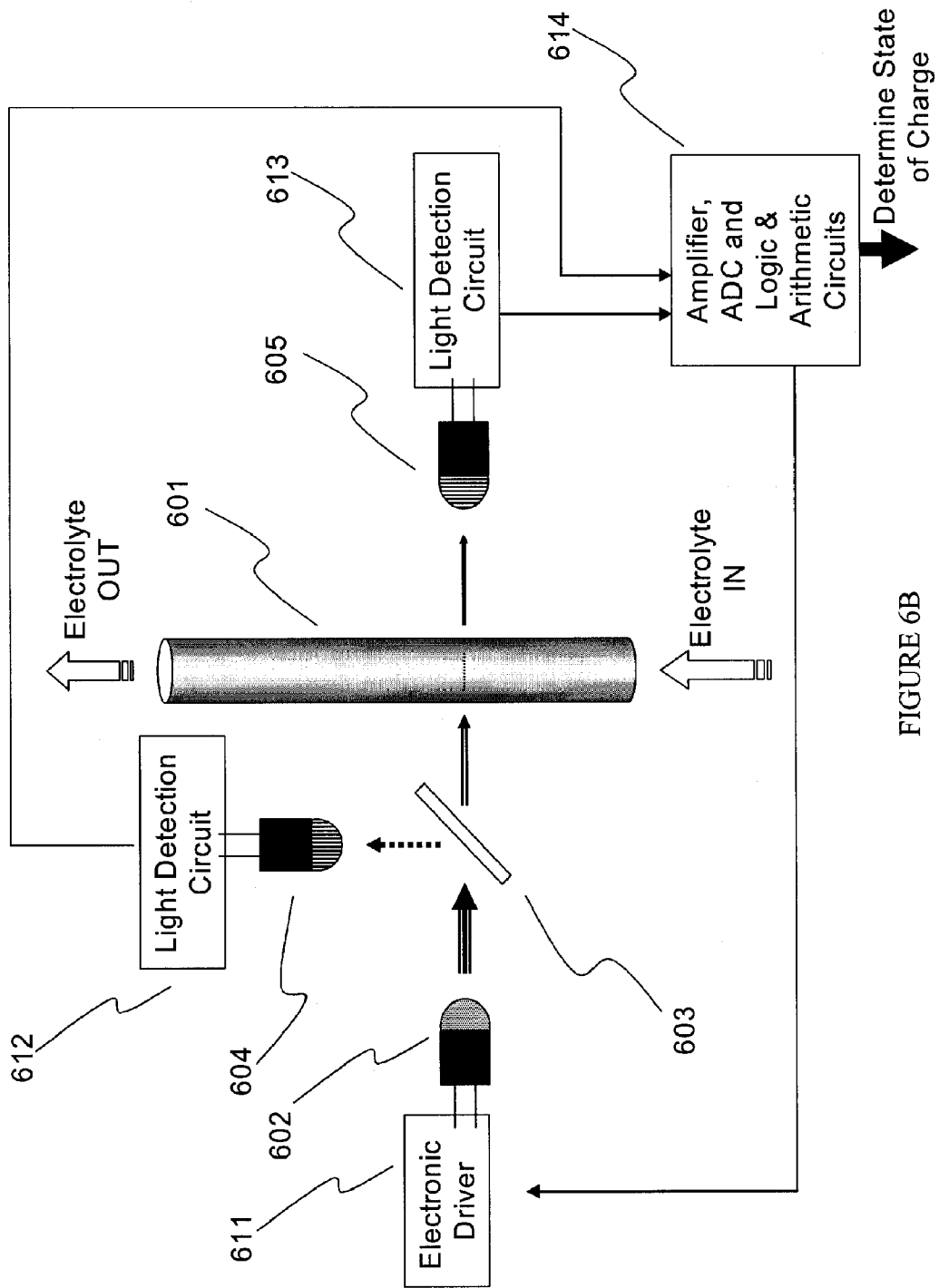
FIG. 6B represents a diagram of a spectrophotometer for use in measuring the charge state of at least one electrolyte, in accordance with one embodiment of the present invention.

FIG. 6B depicts a non-limiting example of the spectrophotometry apparatus as described herein for use in measuring the state of charge of at least one electrolyte of a redox flow battery. A transparent tube 601 carries the electrolyte flow. An LED 602 emits light at a known wavelength, and is driven by an electronic driver 611. It should be noted that light sources are not limited to LEDs, but also include for example lasers, photodiodes, etc. Part of the emitted light is reflected by a partial mirror 603 and is collected and measured by a photodetector 604. A light detection circuit 612 converts the incident light into a measured electrical signal, the amplitude of which monitors the absolute brightness of the light emitter 602 and helps calibrate for any temperature or other systematic dependence effects in the overall detection scheme. The rest of the light emitted by light emitter 602 passes through transparent tube 601, a portion of which will be absorbed by the electrolyte. The transmitted light is captured by photodetector 605 and is measured as an electrical signal by the light detection circuit 613. The two light detection circuits 612 and 613 send their information to a central processing unit 614, which may contain amplifiers, analog-to-digital converters (ADC), logic and arithmetic units. The information from 612 is used as a baseline and as a correction for temperature, time and other systemic dependence of the brightness of the LED and the temperature, time and other systemic dependence of the detectors. Incorporating the correction, the signal from 613 is used to determine the ratio of incident to transmitted light, and then by using Beer's Law, the absorptivity can be calculated. Such methods are well known to those skilled in the art of spectrophotometry. The measured absorptivity is then correlated with previously determined calibration plots and/or calibration tables to determine the state of the charge of the system.

If the state of charge on the two sides of the redox flow battery is different, it indicates that parasitic reactions have taken place. The operator of the battery would then activate a rebalancing mechanism to bring the two electrolytes to a balanced state. As the rebalancing proceeds, the methods described herein would monitor the state of charge and provide active feedback about the progress of rebalancing act.

Rebalancing mechanisms are well known to those of skill in the art. One rebalance mechanism for the Fe/Cr redox storage system involves the direct chemical cathodic reduction of $Fe^{3+}$ ions via reaction with hydrogen generated at the chromium electrode, using a catalyst to speed up the rate of reaction. The catalyst is either activated charcoal made hydrophobic and coated with ruthenium, rhodium, palladium, osmium, iridium, platinum, gold or silver, or tungsten carbide made hydrophobic. (Polytetrafluoroethylene is used to render the metal/tungsten carbide hydrophobic.) The rebalance cell is divided by the catalyst into two chambers, provided on both sides with a support mesh. The catalyst mat separates a hydrogen gas chamber from a liquid chamber for the $Fe^{3+}$ electrolyte, between which a pressure equilibrium is maintained since the separation effect of the porous catalyst mat rests solely on its hydrophobic property. Further details for this rebalance mechanism can be found in U.S. Pat. No. 5,258,241, incorporated herein by reference and other rebalance mechanisms are well known to those of skill in the art.

Processes for accurately and conveniently determining the state of charge of an electrolyte, and subsequently the overall state of charge of a redox system, as described by the methods presented herein, are illustrated in the flowchart shown in FIG. 7. In one embodiment, the processes depicted in the flowchart of FIG. 7 may be implemented using the exemplary spectrophotometry apparatus shown in FIG. 6A or FIG. 6B.

In step 7002, a sample of electrolyte, whose state of charge is to be determined, is obtained from the redox system. In some embodiments, the electrolyte sampling is performed continuously. In other embodiments, the electrolyte sampling is performed periodically. In yet other embodiments, the electrolyte sampling is performed by the initiation of an operator. In yet further embodiments, the electrolyte sampling is performed either continuously, periodically, by operator initiation or by some combination of these methods. Various piping, tubing, valves, etc may be employed in order to acquire the electrolyte sample. In step 7004 the electrolyte is exposed to a light source. Different sources of light can be utilized, such, though not limited to monochromatic, laser, etc. In step 7006 the source light intensity is detected and output as source intensity 7006A. In some embodiments, the light source may be assumed to be at some nominal intensity given the driving voltage and known light source. In other embodiments, the source light intensity is detected by light detection circuit 612 of FIG. 6B where output 7006A is the electrical output from photodetector 604. In step 7008 the sample light intensity is detected and output as sample intensity 7008A. In some embodiments, the sample light intensity is detected by light detection circuit 613 of FIG. 6B where output 7008A is the electrical output from photodetector 605. In step 7010, the light intensities of the source and sample are compared. The true intensity of the transmitted light, after incorporating any corrections, is calculated and the absorptivity is determined, and output as sample absorptivity 7010A. In some embodiments, the circuitry and algorithms for the comparison and calculation are represented by central processing unit 614 of FIG. 6B, which may comprise any or all of components such as analog circuits, ASIC or other mixed signal circuits, amplifiers, analog-to-digital converters (ADC), logic and arithmetic units and other required components as would be known to one skilled in the art of spectrophotometry instrumentation. In step 7012, the state of charge (SOC) is determined by correlating the sample absorptivity 7010A with spectral correlation information as a function of SOC. In some embodiments the spectral correlation information as a function of SOC is in algorithmic form. In other embodiments the correlation information is in the form of lookup tables (as may be derived for example from plots such as those presented in FIGS. 4 and 5).

Figure 7:
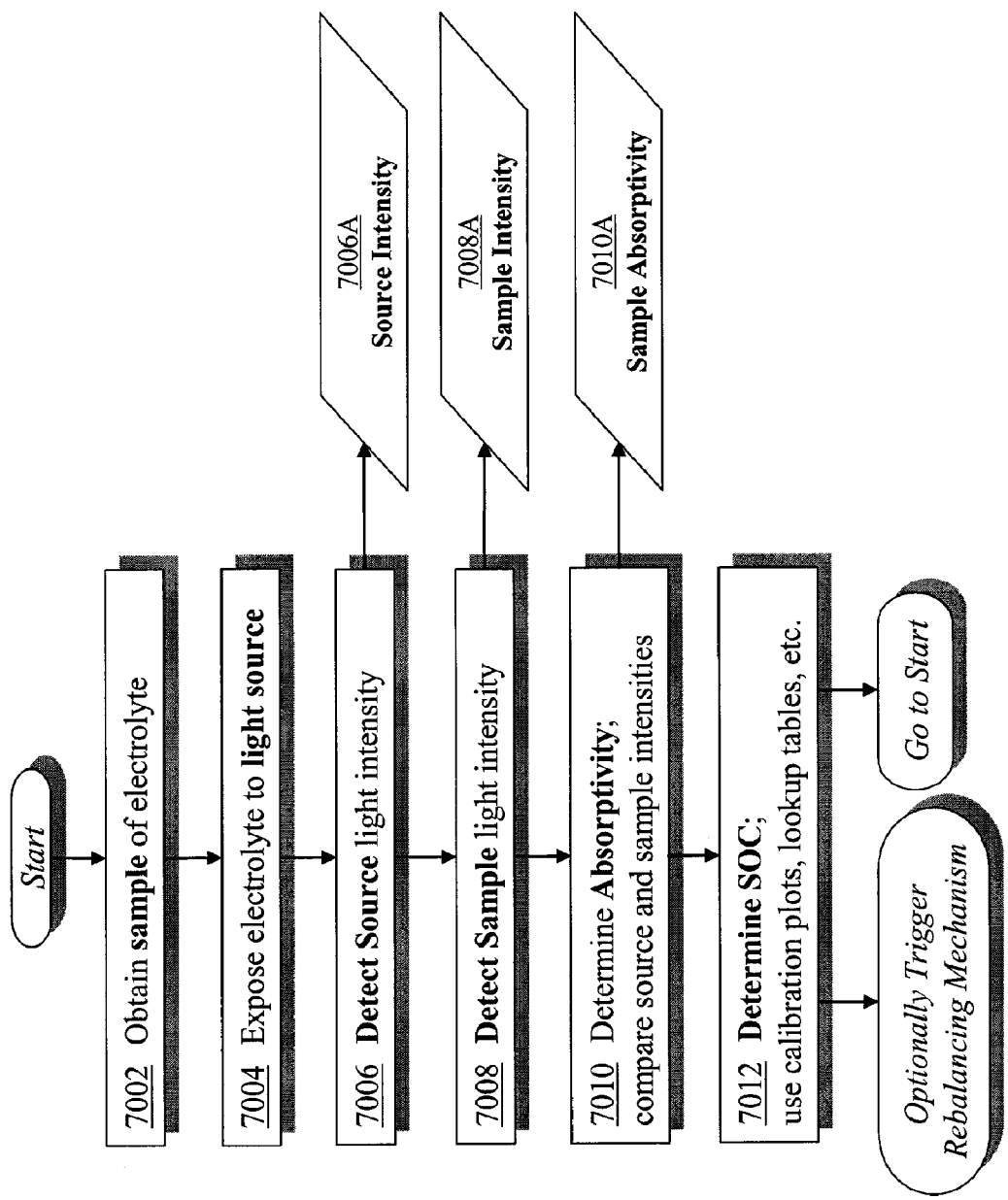
FIG. 7 is a flowchart depicting the various possible processes employed in measuring the charge state of at least one electrolyte, in accordance with one embodiment of the present invention.

Many of the instructions for the steps, and the data input and output from the steps, for the flowchart of FIG. 7, utilize memory and processor hardware components. In some embodiments, the memory storage used to implement the flowchart steps is permanent, such as though not limited to read only memory (ROM). In other embodiments, the memory storage is temporary memory such as though not limited to random access memory (RAM). Memory storage can be any type of memory storage capable of containing program instructions. Such memory storage components will be known to those of skill in art, and include, but are not limited to CD ROM, flash memory, USB drives, etc. Similarly, the processor used to implement the flowchart steps can either be a dedicated controller, an existing system processor, or it can be a dedicated digital signal processor (DSP), as appropriate for the type of step. Alternatively, the instructions may be implemented using some form of a state machine. It should be noted that some of the processes described herein, are presented in terms of procedures, logic blocks, processing, and other symbolic representations of operations on data bits within a computer or digital system memory or on signals within a communication device. These descriptions and representations are the means used by those skilled in the digital communication arts to most effectively convey the substance of their work to others skilled in the art. A procedure, logic block, process, etc., is herein, and generally, conceived to be a self-consistent sequence of steps or instructions leading to a desired result. The steps are those requiring physical manipulations of physical quantities. Usually, though not necessarily, these physical manipulations take the form of electrical or magnetic signals capable of being stored, transferred, combined, compared, and otherwise manipulated in a communication device or a processor. For reasons of convenience, and with reference to common usage, these signals are referred to as bits, values, elements, symbols, characters, terms, numbers, or the like with reference to the present invention.

It should be borne in mind, however, that all of these terms are to be interpreted as referencing physical manipulations and quantities and are merely convenient labels to be interpreted further in view of terms commonly used in the art. Unless specifically stated otherwise as apparent from the discussions herein, it is understood that throughout discussions of the present invention, terms such as "receiving", "measuring", "sensing" or the like, refer to the action and processes of a communication device or a similar electronic computing device that manipulates and transforms data. The data is represented as physical (electronic) quantities within the communication devices components, or the computer system's registers and memories, and is transformed into other data similarly represented as physical quantities within the communication device components, or computer system memories or registers, or other such information storage, transmission or display devices.

The following examples are provided to further illustrate the apparatus and methods described herein, and are not provided to limit the scope of the current invention in any way.

Example 1

Preparation of Correlation Tables (Method 1)

Figure 8:
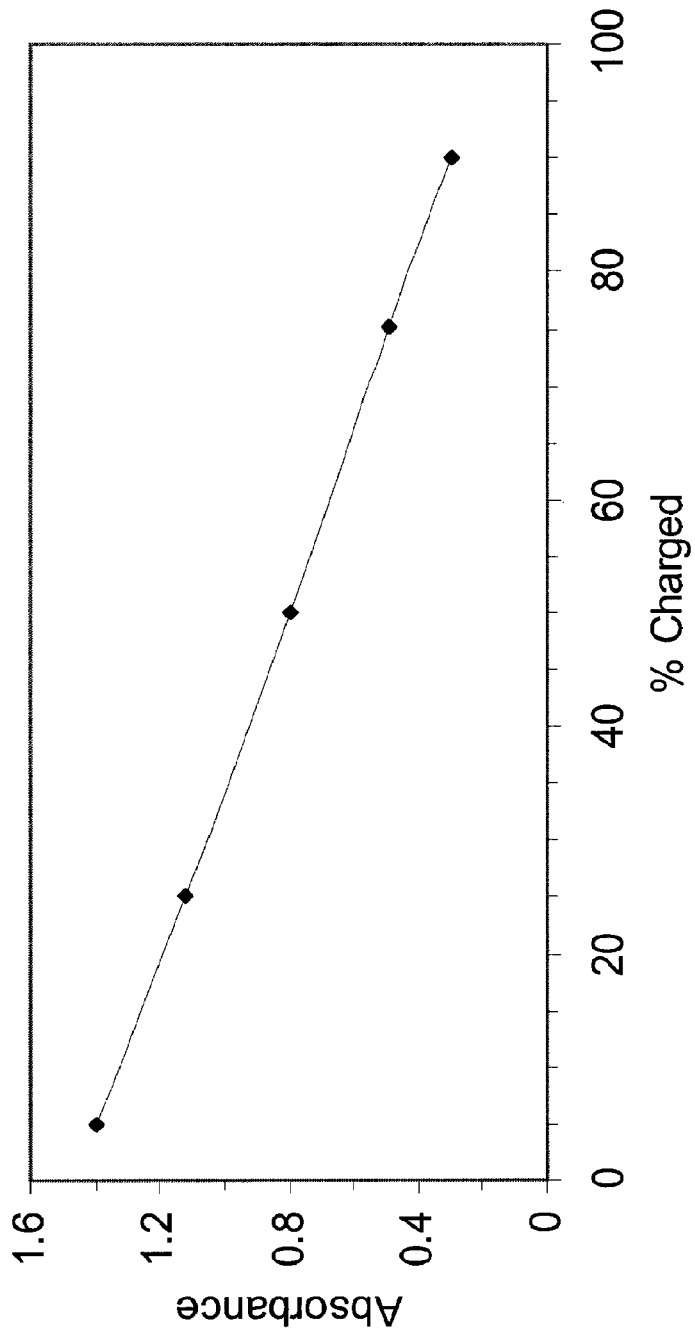
FIG. 8 is a plot of measured absorbance as a function of percentage state of charge for catholyte as described in Example 1.

The absorption spectra of the iron side (Catholyte) of a mixed reactant ($FeCl_2$, $FeCl_3$, $CrCl_3$) half cell were determined for known states of charge/discharge (5% charged, 25% charged, 50% charged, 75% charged and 95% charged) and are shown in FIG. 4. The absorbance at 900 nm for each of the charge states was recorded as shown in the table below, and plotted to form a correlation graph as shown in FIG. 8.

| % Charged | Catholyte Absorptivity (900 nm) |
|---|---|
| 5 | 1.4 |
| 25 | 1.2 |
| 50 | 0.8 |
| 75 | 0.5 |
| 90 | 0.3 |

Figure 9:
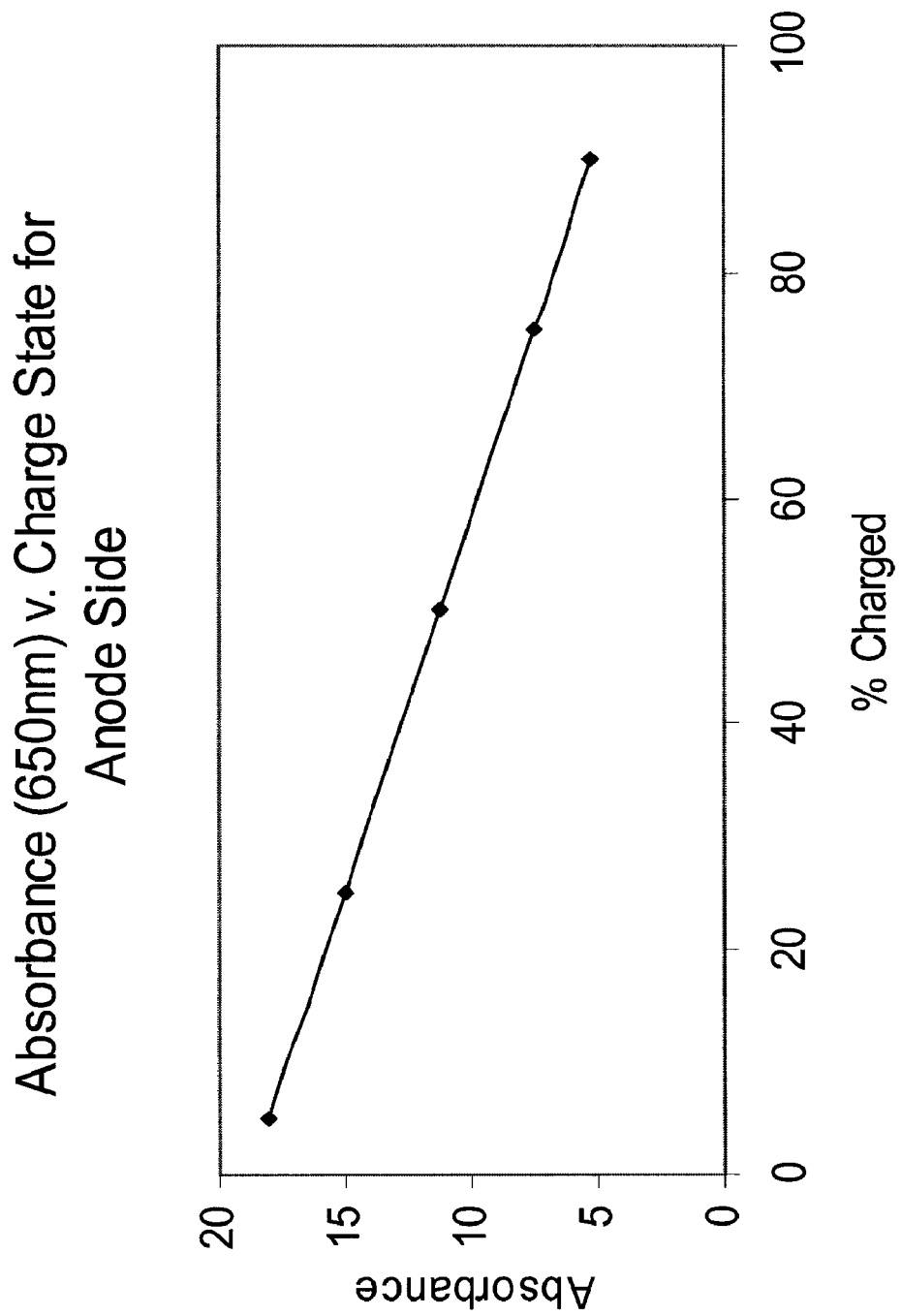
FIG. 9 is a plot of measured absorbance as a function of percentage state of charge for anolyte as described in Example 1.

The absorption spectra of the chromium side (Anolyte) of a mixed reactant ($CrCl_3$, $CrCl_2$, $FeCl_2$) half cell were determined for known states of charge/discharge (5% charged, 25% charged, 50% charged, 75% charged and 0.95% charged) and are shown in FIG. 5. The absorbance at 650 nm for each of the charge states was recorded as shown in the table below, and plotted to form a correlation graph as shown in FIG. 9.

| % Charged | Anolyte Absorptivity (650 nm) |
|---|---|
| 5 | 18 |
| 25 | 15 |
| 50 | 11.25 |
| 75 | 7.5 |
| 90 | 5.25 |

Example 2

Preparation of Correlation Tables (Method 2)

The following solutions are prepared in 1N hydrochloric acid:

| | Molar conc. of species | | | | |
|---|---|---|---|---|---|
| Soln. # | $CrCl_3$ | $CrCl_2$ | $FeCl_3$ | $FeCl_2$ | Corresponds to State of Charge of Electrolyte |
| 1 | 1M | | 1M | | Fully charged catholyte |
| 2 | 1M | | 0.75M | 0.25M | 75% charged (25% discharged) catholyte |
| 3 | 1M | | 0.5M | 0.5M | 50% charged (50% discharged) catholyte |
| 4 | 1M | | 0.25M | 0.75M | 25% charged (75% discharged) catholyte |
| 5 | 1M | | | 1M | Fully discharged catholyte |
| 6 | | 1M | | 1M | Fully charged anolyte |
| 7 | 0.25M | 0.75M | | 1M | 75% charged (25% discharged) anolyte |
| 8 | 0.5M | 0.5M | | 1M | 50% charged (50% discharged) anolyte |
| 9 | 0.75M | 0.25M | | 1M | 25% charged (75% discharged) anolyte |
| 10 | 1M | | | 1M | Fully discharged anolyte |

Therefore:

Solution 1 contains $CrCl_3$ (15.84 g, 100 mmol) and $FeCl_3$ (16.22 g, 100 mmol) in HCl (100 mL, 1N);

Solution 2 contains $CrCl_3$ (15.84 g, 100 mmol), $FeCl_3$ (12.165 g, 75 mmol) and $FeCl_2$, (3.17, 25 mmol) in HCl (100 mL, 1N);

Solution 3 contains $CrCl_3$ (15.84 g, 100 mmol), $FeCl_3$ (8.1 µg, 50 mmol) and $FeCl_2$ (6.34 g, 50 mmol) in HCl (100 mL, 1N);

Solution 4 contains $CrCl_3$ (15.84 g, 100 mmol), $FeCl_3$ (4.055 g, 25 mmol) and $FeCl_2$ (9.51 g, 75 mmol) in HCl (100 mL, 1N);

Solution 5 contains $CrCl_3$ (15.84 g, 100 mmol) and $FeCl_2$ (12.68 g, 100 mmol) in HCl (100 mL, 1N);

Solution 6 contains $FeCl_2$ (12.68 g, 100 mmol) and $CrCl_2$ (12.29 g, 100 mmol) in HCl (100 mL, 1N);

Solution 7 contains $FeCl_2$ (12.68 g, 100 mmol), $CrCl_2$ (9.22 g, 75 mmol) and $CrCl_3$ (3.96, 25 mmol) in HCl (100 mL, 1N);

Solution 8 contains $FeCl_2$ (12.68 g, 100 mmol), $CrCl_2$ (6.15 g, 50 mmol) and $CrCl_3$ (7.92, 50 mmol) in HCl (100 mL, 1N);

Solution 9 contains $FeCl_2$ (12.68 g, 100 mmol), $CrCl_2$ (3.07 g, 25 mmol) and $CrCl_3$ (11.88, 75 mmol) in HCl (100 mL, 1N);

Solution 10 contains $FeCl_2$ (12.68 g, 100 mmol) and $CrCl_3$ (15.84, 100 mmol) in HCl (100 mL, 1N).

The absorptivities of each of these solutions are measured at 800 nm and a plot of absorptivity vs state of charge is plotted for the catholyte and the anolyte. These plots are used as calibration plots.

Example 3

Determination of State of Charge and State of Charge Balance of a Mixed Reactant (Fe/Cr) Redox Flow Cell A mixed reactant redox flow cell is prepared with a $CrCl_3$, $CrCl_2$, $FeCl_2$ chromium side anolyte and a $FeCl_2$, $FeCl_3$, $CrCl_3$ iron side catholyte. The cell is run through five charge—discharge cycles. The absorbance of the anolyte at 650 nm is measured and determined to be 11.2. Using the correlation table in FIG. 9, the anolyte is calculated to be 50% charged (i.e. the state of charge is 50%). The absorbance of the catholyte at 900 nm is measured and determined to be 0.8. Using the correlation table in FIG. 8, the anolyte is calculated to be 50% charged (i.e. the state of charge is 50%). Thus the system is still in a state of charge balance. The cell is next run through an additional twenty charge—discharge cycles. The absorbance of the anolyte at 650 nm is measured and determined to be 11. Using the correlation table in FIG. 9, the anolyte is calculated to be 48% charged. The absorbance of the catholyte at 900 nm is measured and determined to be 0.9. Using the correlation table in FIG. 8, the anolyte is calculated to be 40% charged. Thus, the system is determined to be out of charge balance. A rebalance mechanism is initiated in order to return the system back to a state of charge balance.

In view of the embodiments described herein, the present invention has been shown to provide the apparatus and methods to overcome the limitations of electrochemical measurements of state of charge (SOC) in redox flow batteries, and render individual determinations of SOC of mixed or unmixed electrolytes, thus providing information to the operating mechanism of the flow batteries which might take steps to rebalance the system if individual SOC's are not balanced.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A method for determining the state of charge of a redox flow cell battery, the redox flow cell battery comprising:
    at least one redox flow cell;
    an electrolyte composition comprising one or more metal ions, wherein the metal ions go between an oxidized form and a reduced form during charging/discharging of the redox flow cell battery; and
    at least one tank for holding the electrolyte composition, the tank coupled to the redox flow cell such that the tank supplies electrolyte composition to the redox flow cell during use,
the method comprising:
    providing one or more test samples of the electrolyte composition while electrolyte composition is flowed between the tank to the redox flow cell;
    measuring an optical absorption of one or more of the test samples of the electrolyte composition;
    comparing the optical absorption of the test sample with reference optical absorption measurements of the electrolyte composition in various states of charge to provide a relative absorptivity of the test sample; and
    determining the state of charge of the redox flow cell battery from the relative absorptivity of the test sample.

2. The method of claim 1, wherein of the reference optical absorption measurements of the electrolyte composition in various states of charge is obtained by:
    providing a sample of the electrolyte composition in fully oxidized form;
    measuring the optical absorption spectrum of said pure oxidized electrolyte the electrolyte composition in fully oxidized form;
    providing a sample of the electrolyte composition in fully reduced form; and
    measuring the optical absorption spectrum of the electrolyte composition in fully reduced form.

3. The method of claim 1, wherein the electrolyte composition comprises chromium ions and iron ions.

4. The method of claim 1, wherein the test sample is obtained from at least one tank.

5. The method of claim 1, wherein the test sample is obtained from electrolyte composition flowing between at least one tank and at least one redox flow cell.

6. The method of claim 1, wherein the redox flow cell battery comprises:
    an anolyte tank coupled to an anode half-cell of the redox flow cell battery to supply an anolyte composition to the redox flow cell battery; and
    a catholyte tank coupled to a cathode half-cell of the redox flow cell battery to supply catholyte to the redox flow cell battery.

7. The method of claim 6, wherein the test sample is a sample of the anolyte composition.

8. The method of claim 7, wherein comparing the optical absorption spectrum of said test sample with a reference optical absorption comprises comparing an optical spectrum of the anolyte composition test sample to a reference spectrum of the anolyte composition in various states of charge to provide a relative absorptivity of the anolyte composition test sample.

9. The method of claim 6, wherein the test sample is a sample of the catholyte composition.

10. The method of claim 9, wherein comparing the optical absorption spectrum of said test sample with a reference optical absorption comprises comparing an optical spectrum of the catholyte composition test sample to a reference spectrum of the catholyte composition in various states of charge to provide a relative absorptivity of the catholyte composition test sample.

11. The method of claim 6, wherein a catholyte test sample is a sample of the catholyte composition and an anolyte test sample is a sample of the anolyte composition, and wherein the state of charge of the electrolyte composition is determined from the relative absorptivity of the catholyte test sample and the anolyte test sample.

12. The method of claim 11, wherein the relative absorptivity of the anolyte test sample is determined by comparing an optical spectrum of the anolyte test sample to a reference spectrum of the anolyte composition in various states of charge; and wherein the relative absorptivity of the catholyte test sample is determined by comparing an optical spectrum of the catholyte test sample to a reference spectrum of the catholyte composition in various states of charge.

13. The method of claim 1, wherein the redox flow cell battery further comprises a spectrophotometer optically coupled to a flow line supplying the electrolyte composition to at least one redox flow cell.

14. The method of claim 13, wherein the spectrophotometer comprises one or more light emitters that admit light as photometric beams with spectral bandwidths of less than 50 nm Full Width at Half Maximum.

15. The method of claim 13, wherein the spectrophotometer is coupled to a transparent tube through which the electrolyte composition flows.

16. The method of claim 15, wherein the transparent tube is curved to impart a lensing effect on incident light from the spectrophotometer.

17. The method of claim 1, wherein the electrolyte composition comprises chromium ions and iron ions, and wherein the optical absorption of the test sample is measured at a wavelength between about 700 nm and 1000 nm.

18. A method for determining the state of charge of a redox flow cell battery, the redox flow cell battery comprising:
    at least one redox flow cell comprising an anode half cell and a cathode half cell;
    an anolyte composition comprising chromium ions and iron ion,
    an anolyte tank holding the anolyte composition, wherein the anolyte tank is coupled to the anode half cell such that the tank supplies anolyte composition to the anode half cell during use;
    a catholyte composition; and
    an catholyte tank holding the catholyte composition, wherein the catholyte tank is coupled to the catholyte half cell such that the tank supplies catholyte composition to the catholyte half cell during use;
the method comprising:
    providing one or more test samples of the anolyte composition and/or the catholyte composition;
    measuring an optical absorption of one or more of the test samples;
    comparing the optical absorption of one or more of the test samples with reference optical absorption measurements of the anolyte and/or catholyte composition in various states of charge to provide a relative absorptivity of one or more of the test samples; and
    determining the state of charge of the redox flow cell battery from the relative absorptivity of one or more test samples.

* * * * *